(12) United States Patent
Kress

(10) Patent No.: US 12,329,357 B2
(45) Date of Patent: Jun. 17, 2025

(54) DEVICE AND METHOD FOR CONTAMINATION-FREE PERFORMANCE OF AN ENDOSCOPIC EXAMINATION

(71) Applicant: Jürgen Kress, Essenbach (DE)

(72) Inventor: Jürgen Kress, Essenbach (DE)

( * ) Notice: Subject to any disclaimer, the term of this patent is extended or adjusted under 35 U.S.C. 154(b) by 450 days.

(21) Appl. No.: 16/965,978

(22) PCT Filed: Apr. 26, 2019

(86) PCT No.: PCT/DE2019/100380
§ 371 (c)(1),
(2) Date: Jul. 29, 2020

(87) PCT Pub. No.: WO2019/206381
PCT Pub. Date: Oct. 31, 2019

(65) Prior Publication Data
US 2021/0030261 A1    Feb. 4, 2021

(30) Foreign Application Priority Data
Apr. 27, 2018    (DE) ...................... 10 2018 110 228.3

(51) Int. Cl.
*A61B 1/00*    (2006.01)
*A61B 1/015*    (2006.01)
(Continued)

(52) U.S. Cl.
CPC ...... *A61B 1/00142* (2013.01); *A61B 1/00068* (2013.01); *A61B 1/00091* (2013.01);
(Continued)

(58) Field of Classification Search
CPC ......... A61B 19/00; A61B 46/00; A61B 90/04; A61B 1/00142; A61B 1/0125;
(Continued)

(56) References Cited

U.S. PATENT DOCUMENTS 3,866,601 A * 2/1975 Russell .............. A61B 1/00142
600/114
4,593,699 A * 6/1986 Poncy .................... A61B 50/30
600/459

(Continued)

FOREIGN PATENT DOCUMENTS

EP            1 578 255 A1    9/2005
WO    WO 2009/086396 A1    7/2009

*Primary Examiner* — Michael J Carey
*Assistant Examiner* — Megan Elizabeth Monahan
(74) *Attorney, Agent, or Firm* — DP IP GROUP; Franco S. De Liguori

(57) ABSTRACT

An endoscope with a contamination protection device for protecting the endoscope and a person performing an examination on a patient from contamination. The endoscope has a rigid or flexible shaft, an inner sleeve configured to be unrolled from a rolled-up state over the shaft to cover the shaft in an airtight, watertight and germ-tight manner, and an outer sleeve configured to envelop the inner sleeve. The outer sleeve is connected in an airtight, watertight and germ-tight manner only to a proximal end of the inner sleeve at the proximal end of the shaft and so as to extend beyond the tip of the shaft. The outer sleeve and the inner sleeve
(Continued)

together provide a protection volume between a body orifice of a patient to be examined and a proximal end of the for collecting body fluids released by the patient during the examination.

22 Claims, 19 Drawing Sheets

(51) Int. Cl.
*A61B 1/018* (2006.01)
*A61B 1/31* (2006.01)
*A61B 1/06* (2006.01)

(52) U.S. Cl.
CPC ...... *A61B 1/00096* (2013.01); *A61B 1/00112* (2013.01); *A61B 1/00148* (2022.02); *A61B 1/015* (2013.01); *A61B 1/018* (2013.01); *A61B 1/31* (2013.01); *A61B 1/06* (2013.01)

(58) Field of Classification Search
CPC . A61B 1/015; A61B 1/00091; A61B 1/00094; A61B 1/00148; A61B 1/00112; A61B 1/018; A61B 1/31; A61B 1/06
See application file for complete search history.

(56) References Cited

U.S. PATENT DOCUMENTS

| | | | |
|---|---|---|---|
| 4,646,722 A * | 3/1987 | Silverstein | A61B 1/00142 600/122 |
| 4,907,395 A | 3/1990 | Opie et al. | |
| 5,217,001 A | 6/1993 | Nakao et al. | |
| 5,388,593 A * | 2/1995 | Thomalla | A61B 46/30 128/853 |
| 5,433,221 A | 7/1995 | Adair et al. | |
| 6,357,445 B1 * | 3/2002 | Shaw | A61B 46/30 128/853 |
| 8,241,208 B2 | 8/2012 | Jiang | |
| 8,262,561 B2 * | 9/2012 | Kress | A61B 1/00142 600/156 |
| 9,763,562 B2 * | 9/2017 | Avitsian | A61B 1/00142 |
| 2009/0182198 A1 * | 7/2009 | Skerven | A61B 1/00142 600/121 |
| 2011/0251460 A1 * | 10/2011 | Jiang | A61B 1/00068 600/121 |
| 2014/0051929 A1 * | 2/2014 | Braun | A61B 1/00142 600/125 |

* cited by examiner

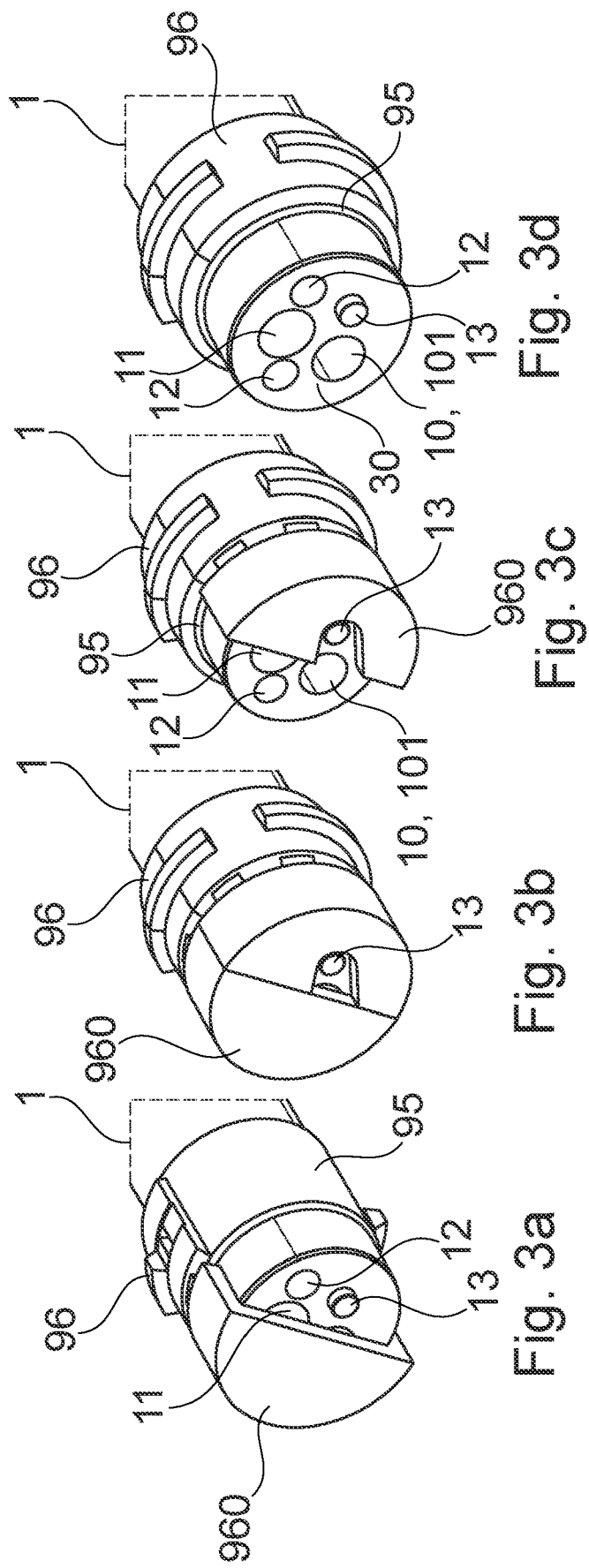

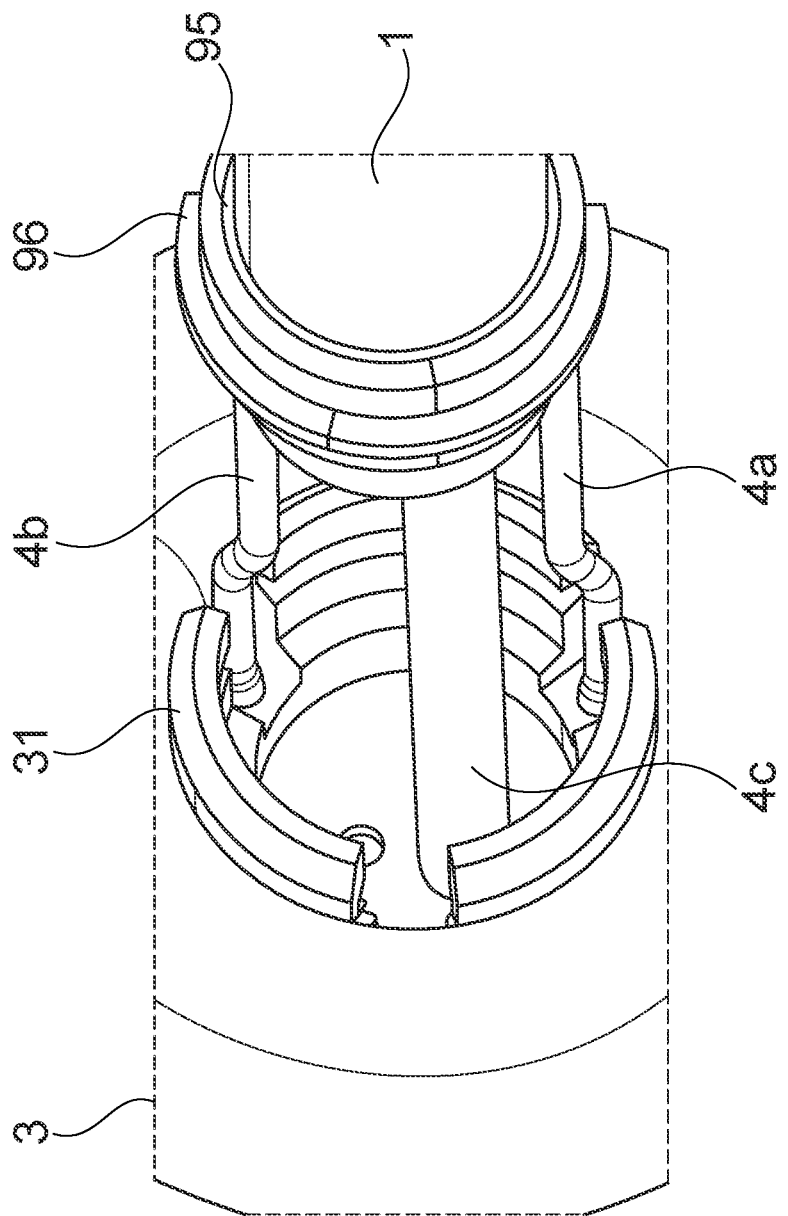

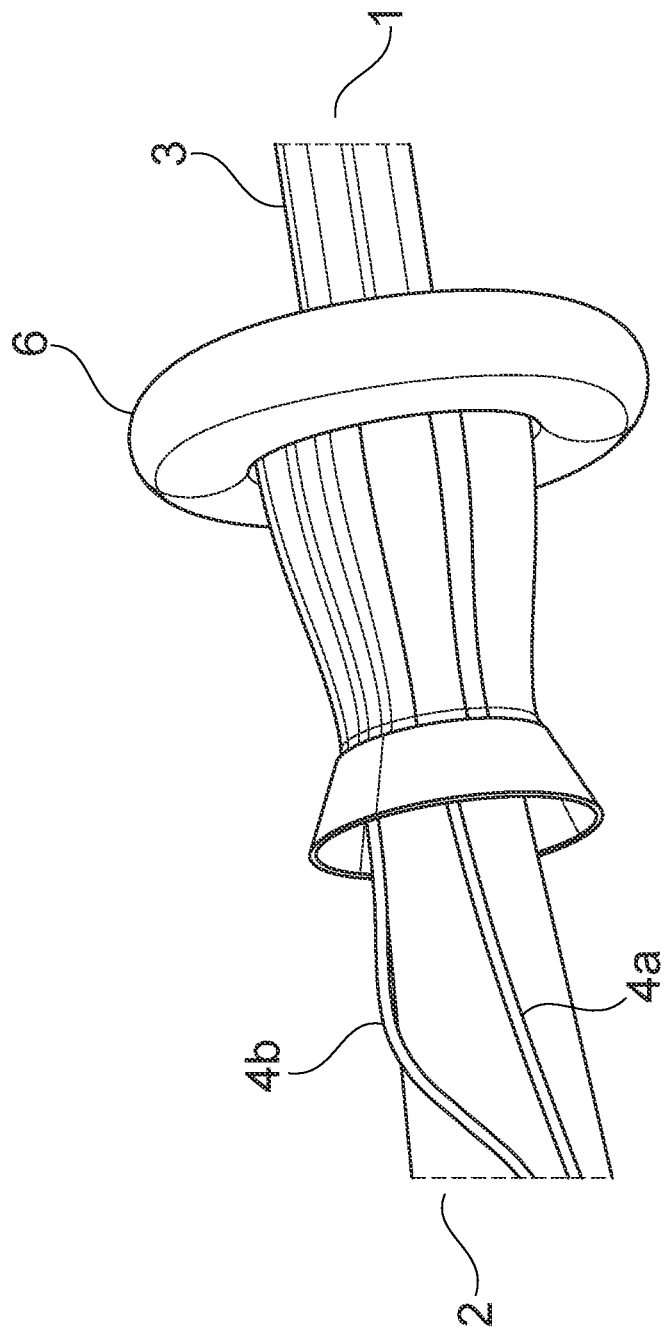

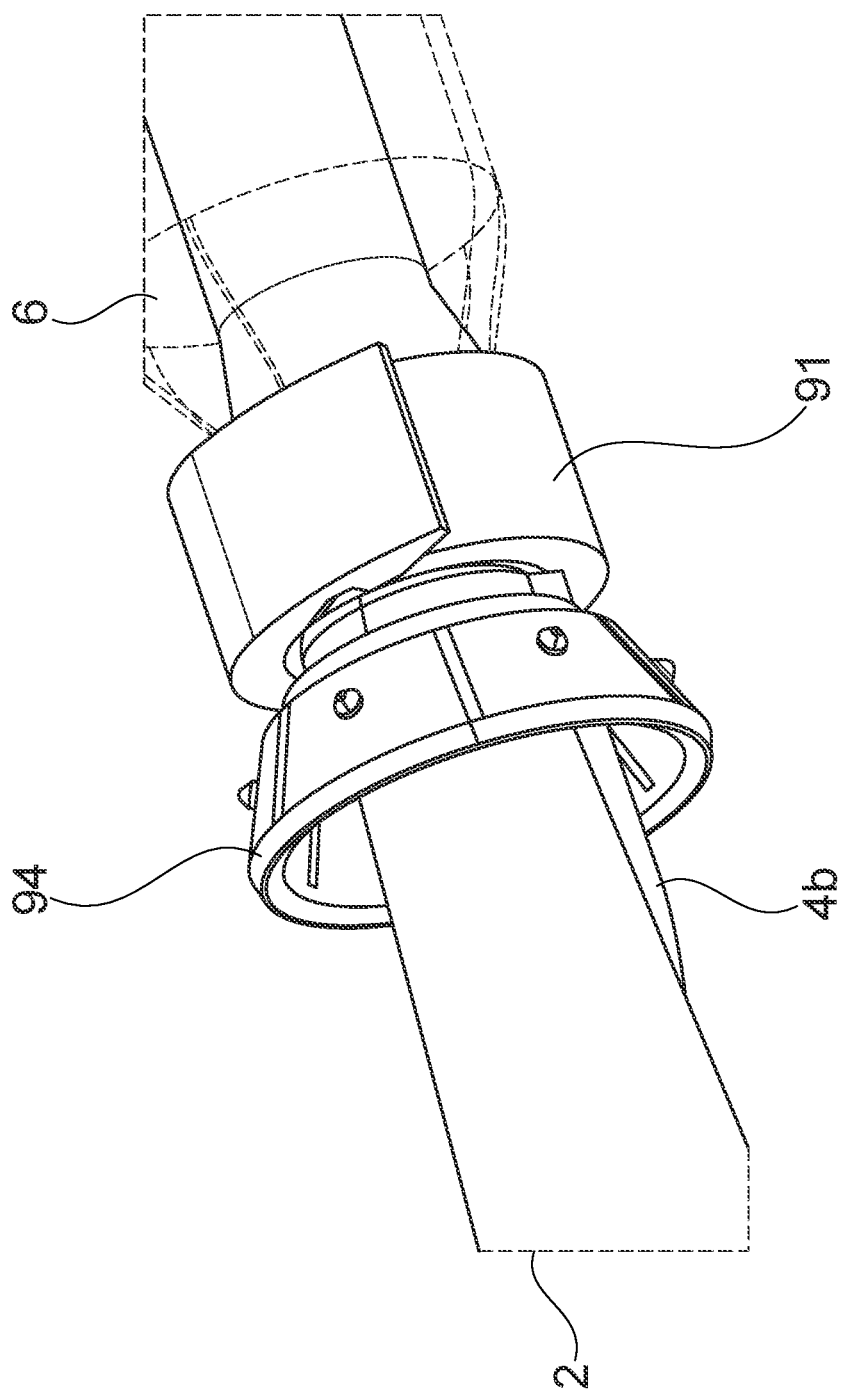

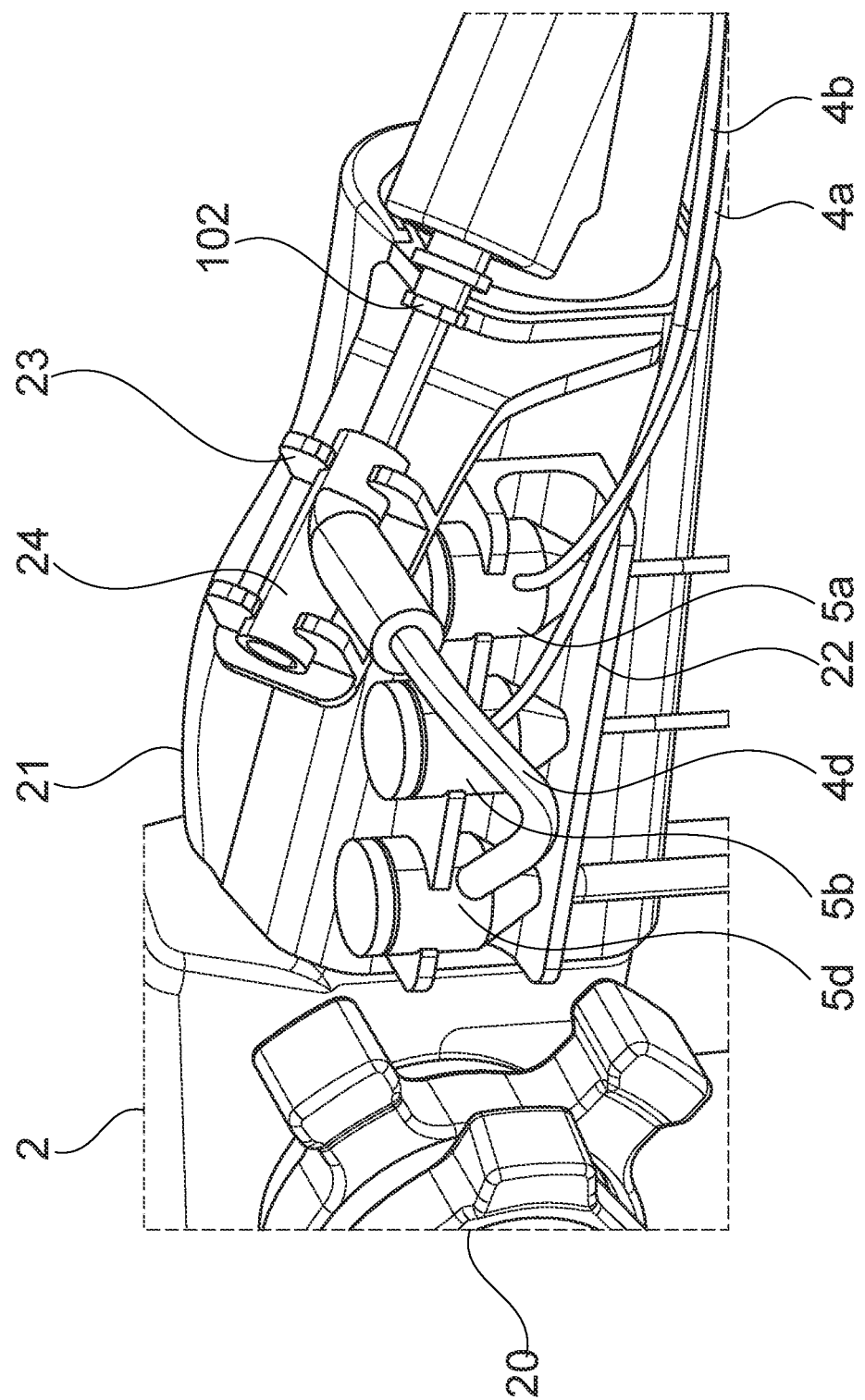

DEVICE AND METHOD FOR CONTAMINATION-FREE PERFORMANCE OF AN ENDOSCOPIC EXAMINATION

BACKGROUND

Field

The present invention relates to an endoscope with contamination protection device.

Background Information

Medical endoscopy is a diagnostic method for investigating body orifices or cavities, in which the possibility of performing minimally invasive surgery is also available. The method is based on introducing an imaging probe into the body orifice to be examined.

For this purpose, endoscopes are used, which consist of a handle and a rigid or flexible shaft that is connected thereon, at the tip of which, devices for illumination and imaging are provided. For lighting, either the light of a light source disposed outside the endoscope is used, which is guided through the glass-fibre bundle running in the interior of the endoscope shaft or, more usually with modern endoscopes, through light generated by means of light sources, in particular LEDs, integrated in the shaft tip. For representing the object to the examined, optics are disposed on the shaft tip, the image from which, in the case of endoscopes of the most modern design, is registered by a video chip, processed and read by means of a data cable that also runs in the shaft.

For manipulation of the object to be examined, in particular for dosed inflation of hollow organs and body cavities, an air nozzle is further provided on the shaft tip, which can be pressurised via a channel running in the interior of the shaft by means of pumps or irrigators disposed outside the endoscope.

Furthermore, on the shaft tip, a water nozzle disposed at an angle, which is used during the investigation for rinsing body secretions from the shaft tip, in particular to clean the imaging optics. The water nozzle is supplied via a water channel running in the shaft interior.

In addition, endoscopes usually have an instrument channel running through the shaft, through which micromechanical devices, such as for-ceps, grippers or loops on Bowden cables are guided into the examination space in order to perform, for example, a biopsy.

In addition, the instrument channel can also be used for suction. For this purpose, it opens at its proximal end in the region of the handle in a Y-shaped manifold piece, which, via its two proximal legs, provides both accessibility for an instrument and a connection means for a pump.

For operation by the examining doctor, valves for air, water and suction are provided on the handle, as well as operating elements for angling and fine positioning of the shaft tip, which is actuated via Bowden cables running in the shaft. The coarse positioning of the shaft in the body orifice to be examined is performed by manual advancement or withdrawal. The operation of the instrument mechanism is performed via a separate operating element provided at the proximal end of the instrument.

In practice, the contamination with body fluids occurring in endoscopic examinations represents a serious problem. Such contamination affects the endoscope, the examination environment, the medical personnel as well as, when an inadequately sterilised endoscope is used, the examined patient himself.

The effort for cleaning and sterilisation of a used endoscope is consider-able. It comprises numerous work steps of mechanical cleaning, rinsing, application of enzyme cleaners, disinfection and drying, and in practice typically takes 45 minutes. The procedure involves high personnel and equipment costs, and represents a decisive factor in the pay-back time of the endoscopes, which are expensive to procure. Furthermore, there is an undesirable capital commitment, since, to ensure continuous examination operation, a large number of endoscopes must be provided.

Besides these economic aspects, in particular the contamination risk represents a serious problem for the medical personnel conducting the endoscopy. Thus, due to the manual sliding of the endoscope shaft during the examination, the treating doctor inevitably comes into contact with body fluids. With instrument removal from the soiled instrument channel, too, the risk of contamination is evident. Likewise, the contamination of the examination environment occurring during examination, in particular the patient table must be noted.

In the prior art, contamination devices for medical endoscopes are known. Thus, patent EP1578255B1 describes a protective sleeve comprising an elastic material, which, starting from its tip, is drawn over the endoscope shaft in the manner of a condom. This sleeve consists, at least in the region of the endoscope optics, of an optically transparent material so as not to impair the endoscopic imaging. Since, with the use of such a protective sleeve, the working channels running in the interior of the endoscope shaft are no longer accessible, the patent teaches the provision of separate air, water and instrument channels, which are to be disposed between the endoscope shaft and protective sleeve and are connected in an airtight, watertight and germ-tight manner, to the protective sleeve. With the use of such a protective device in the prior art, a direct contamination of the endoscope during the examination is avoided.

However, the problem of contamination of the medical personnel and the examination environment remains unsolved, which as a direct consequence can also result in indirect contamination of the endoscope. It is additionally disadvantageous that, by use of a separate external instrument channel, which usually has a not inconsiderable diameter, a significant enlargement of the overall cross-section of the endoscope results, as a result of which endoscopic examination can be associated with severe pains or particular small-sized examination areas may no longer be accessible.

SUMMARY

Against the foregoing background, the present invention wants to achieve the object of ensuring a reliable and comprehensive protection against contamination for endoscopic examination, which drastically reduces or avoids the contamination of the endoscope, the examination environment and the medical personnel, but does not lead to any restriction of the handling and usability of the endoscope.

This is achieved by means of an endoscope with contamination protection device as described and claimed herein.

The essential idea of the present invention consists in providing a protection volume between the patient's body orifice to be examined and the proximal end of the introduced endoscope shaft, which collects all the body fluids released in the course of the examination and keeps them away from contact with the environment. This volume is limited by an inner sleeve, which essentially corresponds to the protective sleeve on the endoscope shaft described in the prior art, as well as by a larger dimensioned outer sleeve, which is fastened on the proximal end of the inner sleeve of the same in an airtight, watertight and germ-tight manner. During the endoscopic examination, only the inner sleeve is introduced into the body orifice to be examined, so that all the body fluids and other contamination adhering to the inner sleeve on drawing out of the endoscope are protectively covered by the outer sleeve.

Advantageous embodiments of the endoscope according to the invention with contamination protection device are described below, which can be combined with one another in a suitable form.

To close off the protection volume, which according to the invention is spanned by the outer and inner sleeves, completely from the examination environment, suitable means are provided at the distal end of the outer sleeve. These consist of connection pieces, which can be connected to devices according to the invention that are provided at the patient side.

For coloscopic examination of the intestine, such a device is represented by special diaper pants for the patient to be examined, which have an opening with a receiver part to which the connection piece of the outer sleeve can be connected in an airtight, watertight and germ-tight manner. In this manner, the protection volume is expanded with a section of the diaper pants and, with a snug, leaktight fit of the diaper pants on the patient, is essentially closed off from the examination environment.

By analogy, in the case of gastroscopic examinations of the oesophagus or of the stomach, a suitable bite ring for receiving the connector of the outer sleeve can be used, on which a connection part according to the invention is integrally formed. To avoid a contamination of the outer side of the outer sleeve by body fluids escaping from the corners of the patient's mouth, such a bite ring can be expanded around the jaw part in the manner of a mask, care being taken that no significant impairment of the patient's breathing is thereby involved.

Alternatively, a suitable dimensioned partition wall can be positioned between the patients and the medical staff performing the examination. Thereon, an opening that is disposed such that it fits relative to the patient table is to be provided, which is provided with a receptacle part for connection to the connection piece of the outer sleeve. With such a construction, the direct examination environment, in particular the patient table, will be exposed to contamination during the examination, but not the medical staff on the other side of the partition wall. With a suitable design of the partition wall, in particular in the form of a cabin, the contaminated volume can be further restricted or entirely closed off.

The joining of the connection part and connection piece is to be made airtight, watertight and germ-tight in all the aforementioned embodiments, and secured against accidental opening during performance of the endoscopy. For this purpose, suitable screw, plug, clamp or magnetic connections are known.

As an additional protective measure, the outer sleeve can be further led beyond the proximal end of the inner sleeve and also envelop the handle of the endoscope together with the handle attachment.

The inner and outer sleeve should be made of a material that is conventionally used for medical purposes, which is airtight and watertight as well as impervious to pathogens. It must further have an adequate degree of resistance to mechanical wear such as tearing or abrasion, as well as chemical resistance to substances encountered in the course of endoscopic examination, for example acids or fats. For purposes of assembly, the inner and outer sleeve should be in particular easy to roll up. As suitable polymeric material, polybutene (PB) or cycloolefin polymers (COP) come into consideration.

For contamination protection of the instrument channel running in the interior of the endoscope shaft, the present invention teaches, in an advantageous embodiment, the use of an operating tube, which lines the instrument channel along its entire length and, behind the proximal end of the shaft, projects out of the instrument channel opening, which, in normal commercial endoscopes without contamination protection, serves for introducing the instruments, that is to say not for suction. At the distal end of the inner sleeve, the operating tube opens at its end in an operating tube opening, onto which it is seamlessly integrally formed.

To be able to use the operating tube both for passage of the device as well as for suction, it opens, according to the invention, behind the proximal instrument channel opening in a Y-shaped two-way tube manifold, which is plugged into a suitable receptacle on the holder of a handle attachment or alternatively directly on the proximal instrument channel opening.

The handle attachment of the first variant can further comprise fastenings for the valves, that is to say the air valve, water valve and the suction valve. In the second variant, it is proposed to equip the tube manifold by means of an axially displaceably mounted ring nut, with which the tube manifold can be detachably fastened on the Luer-lock connection, which is usually present, of the proximal instrument channel end.

The operating tube opens in the distal end of this tube manifold such that it is accessible by means of one of the two proximal legs of the tube manifold for an instrument and by means of the other leg for suction.

The suction, in the first variant, is monitored by means of a suction valve that is also provided on the holder of the handle attachment and is connected via a suction tube to a proximal end of the two-way tube manifold.

For endoscopes with more than one instrument channel, for example endoscopes with two instrument channels are known, the contamination protection according to the invention also has more than one operating tube, in particular one operating tube per instrument channel of the endoscope.

Likewise, more than one water or air tube may be present. For example, endoscopes with an additional water channel are known, also described as jet channel, which opens freely in the endoscope tip and is not intended for rinsing the optics but for rinsing the surgery or examination point with water. For such endoscopes, the contamination protection according to the invention can be complemented with a further water tube plus valve. Alternatively, the water tube may also be double barrelled, one barrel being used for rinsing the optics and the other as a jet channel.

In this manner, an internal contamination protection of the endoscope shaft is realised, which permits an unrestricted use of the instrument channel for passing through micromechanical devices and for suction.

In a further embodiment, in which the outer sleeve is continued as a redundant protective measure beyond the proximal shaft end and envelops the handle and attachment, the two-way tube manifold is integrated into the outer sleeve, that is to say is welded thereon so as to be airtight, watertight and germ-tight.

In a further advantageous embodiment, an instrument protection according to the invention is connected on that proximal end of the two-way tube manifold that is provided for introducing an instrument protection according to the invention. This serves for drawing the instrument, which, after completion of the instrument process, was drawn out of the working channel, together with the associated Bowden cables and any tissue sample taken, into a protective instrument tube and thus preserving medical staff and the examination environment against contact with adhering contaminants. The length of this instrument tube is consequently to be dimensioned greater than the length of the operating tube, such that there is space for the entire contaminated section of the instrument and of the Bowden cables therein. The two ends of the instrument tube are in each case provided with a cap with end-face opening, which serves for connecting to the two-way tube manifold and/or to a handle-piece of the instrument. The instrument tube should consist of a material that can be telescoped like a bellows, so that the entire instrument protection can be compressed to a small size, which ensures a clear and compact mounting on the handle attachment.

For fastening the inner sleeve on the tip of the endoscope shaft, the present invention teaches advantageously to embody the distal end section of the inner sleeve in the form of a stiff cap, which is plugged onto a clamping bracket, which comprises the outer surface of the endoscope shaft.

The plug connection is created in that a spring, which surrounds the clamping bracket, engages in a corresponding groove on the inside of the cap. To be able to easy and quickly release the cap again, a yoke-like gripper that extends over a part of the shaft circumference can be integrally formed on it, by means of which, with corresponding force exertion, the circumference of the open end face of the elastic cap can be enlarged to the extent that it can be released again from the spring of the clamping bracket and pulled off the shaft tip.

Alternatively even without using a clamping bracket, the cap can be clamped on the shaft tip with the aid of axially running elastic branches that are integrally formed on the open end face of the cap.

For the passing through of air and water tubes in a space-saving manner, the spring should have corresponding recesses and, in an advantageous embodiment, the tubes should be guided into the cap interior and open into openings on the end face.

The clamping bracket fixing the cap should be underlaid by a gasket which may consist, for example, of silicone, Teflon, EPDM rubber or a self-adhesive material.

In a further advantageous embodiment, the inner and outer sleeves are fastened on the proximal end of the endoscope shaft. For this purpose, a further clamping bracket may be used, on which the inner and outer sleeves are lie and are fixed by a surrounding clip.

Neither the proximal nor the distal clamping bracket needs to be removed between two contamination-protected examinations, as a result of which the time required for preparation of the endoscope for a further examination is advantageously shortened.

It is furthermore advantageous to produce the inner and outer sleeve in one part such that they can be connected to one another at the proximal end of the inner sleeve. Such a connection can be implemented during production or by a welding process, for example the ultrasound welding used for connecting polymeric materials. By this means, a potential weakness regarding the leak-tightness of the protection device is eliminated and the mounting of the sleeves on the endoscope shaft is facilitated.

For easier mounting or dismounting of the contamination protection device, the inner sleeve along the endoscope shaft is advantageously underlaid by a flexible fabric tube.

The steps necessary for mounting and dismounting the contamination protection device on an endoscope are given in detail below within the scope of the description of the figures.

With the use of an endoscope according to the invention, it is advantageous to check the contamination protection device for leak-tightness. Such a leak test may be performed, first, after successful mounting of the device on the endoscope in order to reveal possible material and assembly defects.

A suitable method of leak testing would be, for example, the differential pressure method. The distal end of the outer sleeve with the connection piece, which may be integrally formed thereon, is to be connected to the test device, so that the leak test applies to the protection volume spanned between the inner and outer sleeve. To this end it is also necessary to seal the air and water tube, for example by means of suitable plugs.

With the use of an embodiment of the contamination protection device with operating tube, such a sealing plug should be plugged into the proximal tube end so that, in the course of the leak test, the instrument channel, which is lined by the operating tube, in the endoscope shaft is also checked.

It is furthermore advantageous, even after conclusion of the endoscopic examination, to perform a corresponding leak test. Thereby, it can be examined whether the endoscope has been contaminated in the course of the examination and corresponding cleaning measures are to be performed before the next use. Before the leak test, the outer sleeve, as well as the air, water and, possibly, operating tubes in the region of the handle, are to be cut at their distal end such that the cut ends are sealed air tight. This can be performed by means of a torch cutter.

With the use of an embodiment of the contamination protection device with inner and outer sleeves produced in one piece, the leak test following the examination may also be performed on the already dismounted contamination protection device.

As access for the leak test unit to the contaminated volume of the contamination protection device, in an advantageous embodiment, the proximal end of the operating tube should be used, which, for this purpose, must be opened again. If, in a simpler embodiment of the contamination protection device, no operating tube is present, another opening can be cut into the outer sleeve instead as access.

BRIEF DESCRIPTION OF THE DRAWINGS

Further properties, features and advantages of the present invention are given below with reference to the figures of exemplary embodiments described in greater detail. These are only intended to illustrate the invention, and in no way to limit it.

wherein:

FIGS. 3a-d shows the mounting of the distal clamping bracket;

FIG. 5a-c shows the mounting of the contamination protection device on the proximal shaft end;

FIG. 6a-c shows the mounting of the contamination protection device on the handle;

FIG. 1 shows an overall view of an advantageous embodiment of the endoscope according to the invention with contamination protection device. The distal end of the inner sleeve 3 lying on the endoscope shaft 1 is formed by the cap 31 with the end face 30. On the end face 30, there are disposed the air-tube opening 30a, the water-tube opening 30b and the working-tube opening 30c. The air and water tubes 4a, 4b, which are connected to the air and water-tube openings 30a, 30b are led from the interior of the cap 31, through the openings present in the outer surface thereof, to the outside of the endoscope shaft 1. Starting from the end face 30, the inner sleeve 3 is integrally formed on the outer surface of the cap 31 and covers the openings on the cap 31 which are provided for passage of the air and water tubes 4a, 4b, as well as, furthermore, the entire endoscope shaft 1 together with air and water tubes 4a, 4b running thereon. A sealing of that part of the endoscope that is to be introduced into the body orifice of a patient that is to be examined is thus ensured, which is thereby completed in that the instrument channel 10 that runs in the interior of the endoscope shaft 1 is lined by the working channel that is connected to the working channel opening 30c. The endoscope shaft that is sealed in this way is enveloped by the outer sleeve 6 so that the interspace forms a protective volume in which, during the endoscopic examination, body fluids escaping from the patient's body orifice are intercepted. At the patient side, this protection volume is sealed by means of a connection piece 61 which is provided on the outer sleeve 6, and can be connected to suitable diaper pants 7a or a bite ring 7b. The sealing of the protection volume at the proximal end of the endoscope shaft 1 is ensured in the embodiment shown in FIG. 1 by the clip 91, which, in the inner and outer sleeve 3, 6, presses on a proximal clamping bracket 93 located beneath it. The ends of of the inner and outer sleeves 3, 6 that project beyond this are taken up in the clamp 94 and thus secured, for example, against tearing. For passing air and water tubes 4a, 4b beyond the proximal end of the protection volume, corresponding slits are provided in the proximal clamping bracket 93 located under clip 91, outer and inner sleeve 6, 3. The handle attachment 21, with the valve holder 22 and the instrument holder 23, is mounted on the handle 2, into which the air, water and suction valve 5a, 5b, 5d as well as the two-way tube manifold 24 are plugged. The two-way tube manifold 24, which is connected with its distal end to the operating tube 4c projecting from the proximal instrument channel opening 102 permits, via its two proximal ends, access to the instrument channel 10. The proximal leg of the tube manifold 24, which forms the straight-line extension of the distal leg is provided for an instrument 80 passed through on a Bowden cable, by means of which minimally invasive surgical interventions and biopsies can be performed. On the angled legs of the tube manifold 24, the suction tube 4d and the associated suction valve 5d are connected. Air and water valve 5a, 5d are connected to the air and water tubes 4a, 4b leading to the distal end of the endoscope shaft. The tubes leading out of the valves 5a, 5b, 5d of the endoscope are connected to suitable devices for application of low or high pressure or water, which are not loaded within the scope of the present invention.

FIG. 2 shows a detail view of the distal end of an advantageous embodiment of the endoscope according to the invention. Beneath the optically transparent end face 30 of the inner sleeve 3 or of the cap 31, the lighting devices 12 can be found, the optics 11 used for imaging, as well as the nozzle 13, which is not operated with the use of the endoscope according to the invention. The end face 30 is penetrated by the air tube 4a, which opens in the air tube opening 30a, the water tube 4b with the water-tube opening 30b, as well as the operating tube 4c, which runs in the instrument channel 10, with the operating tube opening 30c. Furthermore, FIG. 2 shows the distal clamping bracket 96, which, underlaid by the distal gasket 95, encloses the outer surface of the endoscope shaft 1 and acts as a receptacle for the cap 31 that is plugged thereon.

With reference to FIGS. 3 to 6, details of a particularly advantageous embodiment of the endoscope according to the invention are shown, and the steps necessary for mounting the contamination protection device are illustrated.

FIGS. 3a to 3d show the assembly of a clamping bracket 96 at the distal end of the endoscope shaft 1. To ensure correct seating of the cap 31 to be mounted thereon, during assembly of the clamping bracket 96, both its axial and radial positioning on the outer surface of the endoscope shaft 1 are of importance. It must be ensured that the end face 30 of the cap 31 is spaced from the end face of the endoscope shaft such that, first, it does not cause a significant restriction of the angle of view of the endoscope optics 11, but, second, there is sufficient space to lead air and water tubes 4a, 4b from the outside of the endoscope shaft 1 to the end face 30 of the cap 31. Furthermore, it must be ensured that the operating tube opening, which in an advantageous embodiment is disposed on the end face 30 of the cap 31, in line with the instrument channel opening 101 on the end face of the endoscope shaft. Furthermore, the air and water tube openings 30a, 30b must not cover or shade the lighting devices 12 on the shaft tip. The present invention therefore teaches the advantageous use of a positioning aid 960 for the assembly of the clamping bracket 96, as illustrated in FIGS. 3a to 3d. The positioning aid 960 is connected to the clamping bracket 96 via predetermined breaking points and is broken off after successful assembly. The essential elements of the positioning aid 960 are a pin, which is disposed on the end face and faces into the interior, and is inserted into the instrument channel opening 101, as well as an end-face opening, which is placed over the nozzle 13, which projects out of the shaft tip. Thereby, the radial orientation of the positioning aid, together with clamping brackets fastened thereon, is clearly fixed and it is ensured that the recesses provided for passing through air and water tubes 4a, 4b are correctly positioned in the spring, which surrounds the clamping bracket in the sense described at the outset. The axial position of the clamping bracket 96 is fixed in that the positioning aid 960 is pressed in an interlocking manner onto the end face of the shaft tip.

The clamping bracket 96 and positioning aid 960 are advantageously embodied in two parts in each case and the connection between the two is produced by means of a clamp-like engagement.

Figure 1:
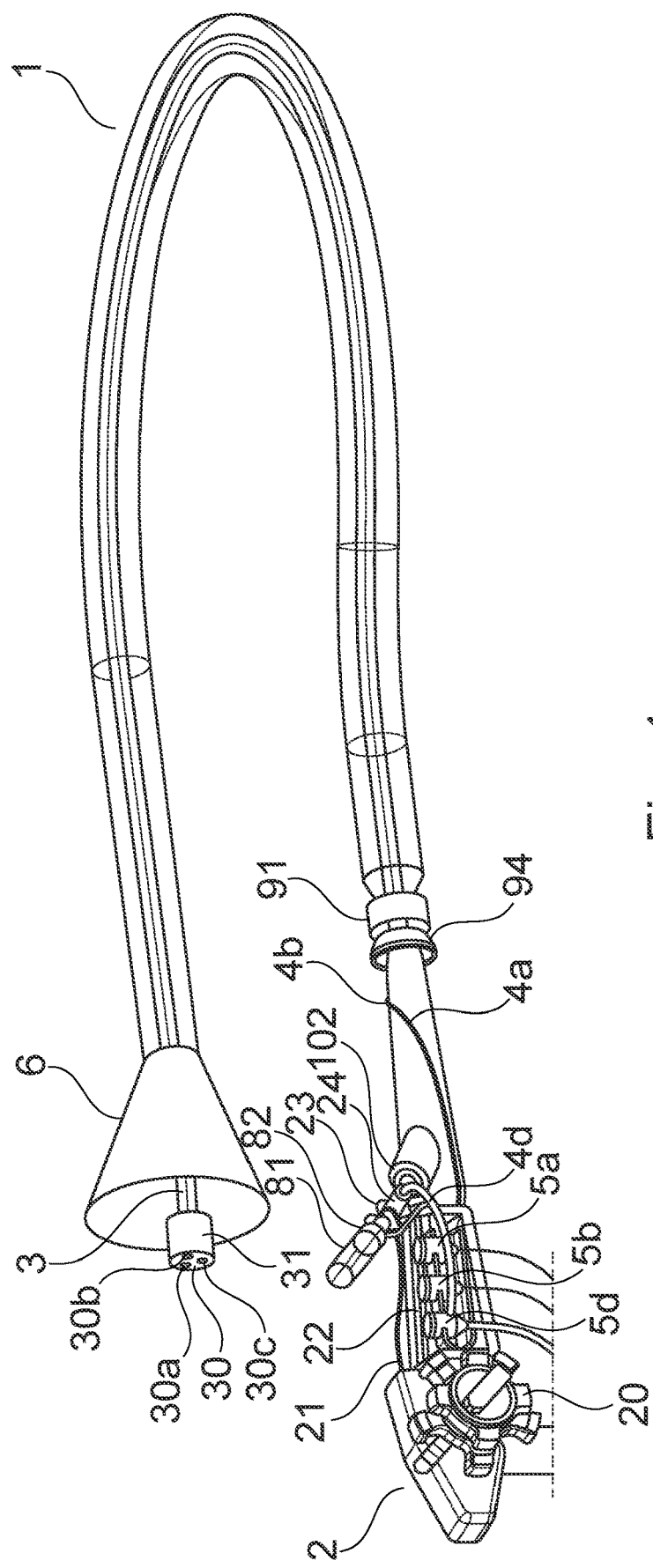
FIG. 1 shows an overall view of an endoscope according to the invention.
Figure 2:
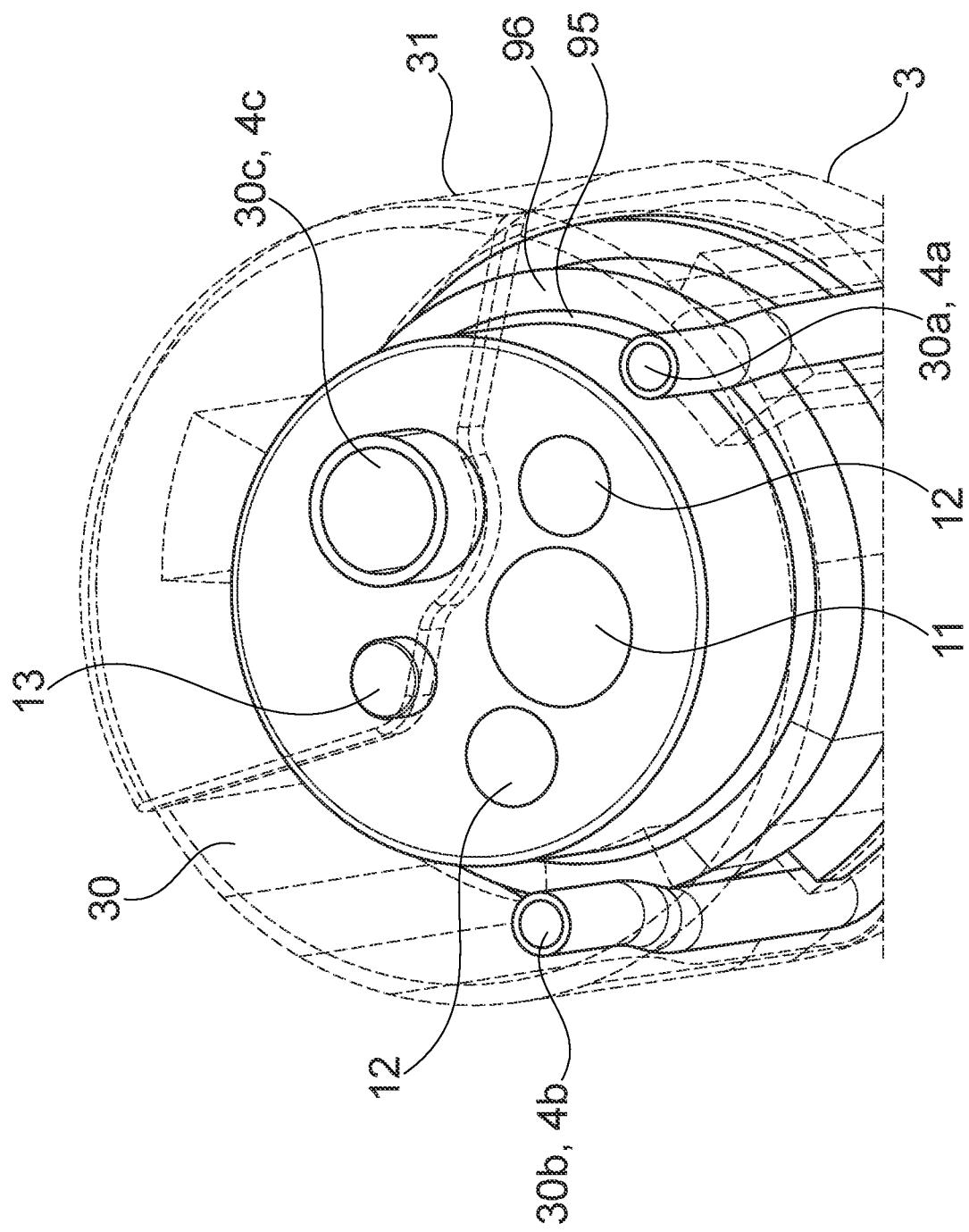
FIG. 2 shows a detail view of the tip of an endoscope according to the invention.
Figure 4A:
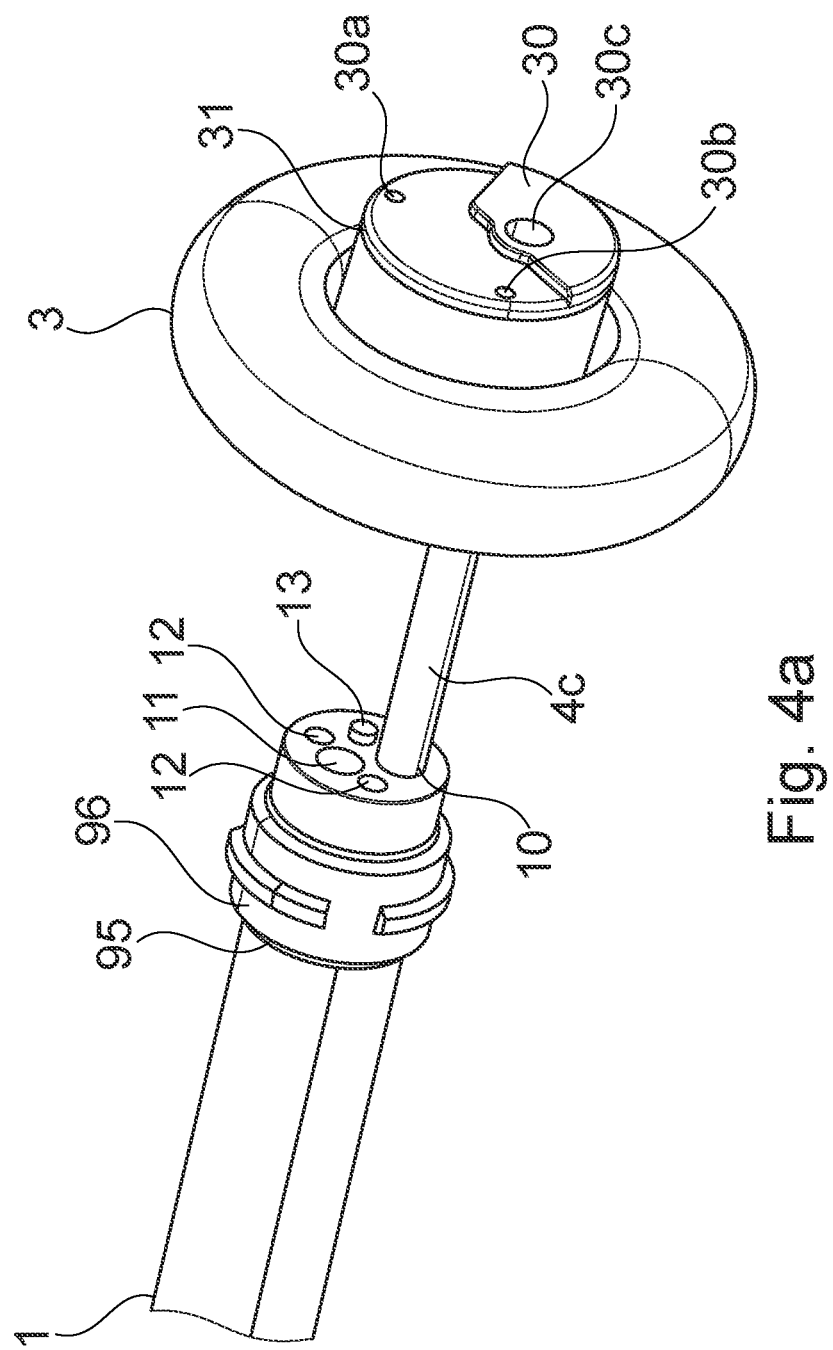
FIG. 4a,b shows the mounting of the distal end of the inner sleeve.

FIG. 4a shows a detail view of the distal end of the endoscope shaft 1 during the assembly of an embodiment of a contamination protection device according to the invention. The inner sleeve 3 is therein first rolled up as far as the cap 31. The operating tube 4c is introduced into the instrument channel 10 in the endoscope shaft 1 and the air and water tubes 4a, 4b, which are not shown here, are shifted on the outside of the shaft 1. The distal gasket 95 and the distal clamping bracket 96 are, as shown in FIGS. 3a to 3d, mounted around the endoscope shaft 1.

FIG. 4b shows a view of the same assembly situation from the opposite perspective. The groove embossed into the cap 31 can be seen therein, into which the spring surrounding the clamping bracket 96 engages for the purpose of connection.

Figure 5A:
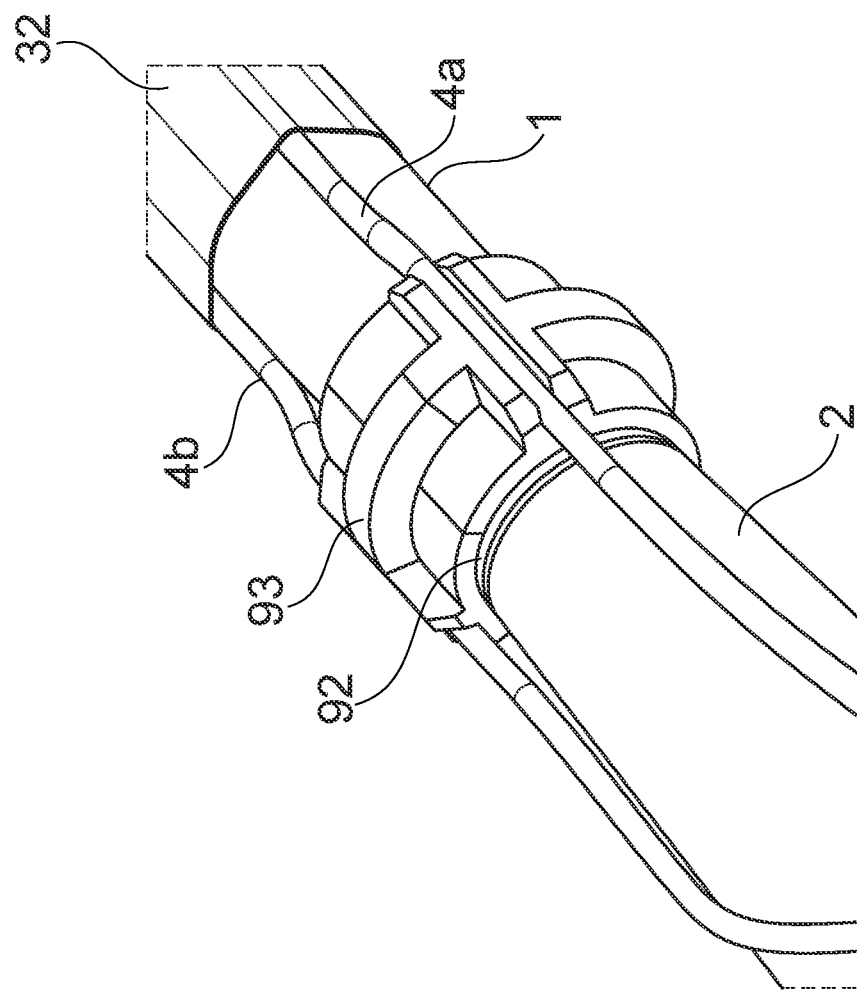

FIG. 5a shows the mounting of an advantageous embodiment of a contamination protection device according to the invention on the proximal end of the endoscope shaft 1. It shows the proximal clamping bracket 93 on the gasket 92 as well as the air and water tubes 4a, 4b, for the passage of which corresponding recesses are provided on the clamping bracket 93. At the upper edge of the figure, the fabric tube 32 is shown, which firmly envelopes the endoscope shaft 1 together with the air and water tubes 4a, 4b running thereon, and forms an underlay for the inner sleeve 3 to be unrolled.

In FIG. 5b, the inner sleeve 3 is completely unrolled over the endoscope shaft 1 such that it also covers the proximal clamping bracket 93. Furthermore, the outer sleeve 6, in a rolled up condition, has been pushed up over the inner sleeve 3, also as far as the proximal clamping bracket 93. With the use of such an embodiment in which the inner and outer sleeve 3, 6 are produced in one part, that is to say, for example welded to one another, the assembly is simplified in that the outer sleeve 6 does not have to be separately pushed up over the inner sleeve 3 as far as the proximal shaft end, but this has already been performed during the unrolling of the inner sleeve 3.

FIG. 5c the interlocking fixing of the inner and outer sleeve 3, 6, with the aid of the clip 91, which presses the two sleeves onto the proximal clamping bracket 93, which is located below. The free ends of the inner and outer sleeves 3, 6, which project beyond the clip 91 are additionally held together by the clamps 94 and, for example, protected against accidental tearing. Subsequent to the fixing on the proximal shaft end in this manner, the outer sleeve 6 is unrolled as far as beyond the distal shaft end.

Neither the proximal clamping bracket 93 nor the distal clamping bracket 96 has to be removed between two contamination-protected examinations. That is to say the time required until preparation of the endoscope for a further examination is advantageously reduced in that after the dismounting of the contamination protection the clamping brackets, together with the gaskets located below remain on the shaft and are used for fastening a further contamination protection.

Figure 6A:
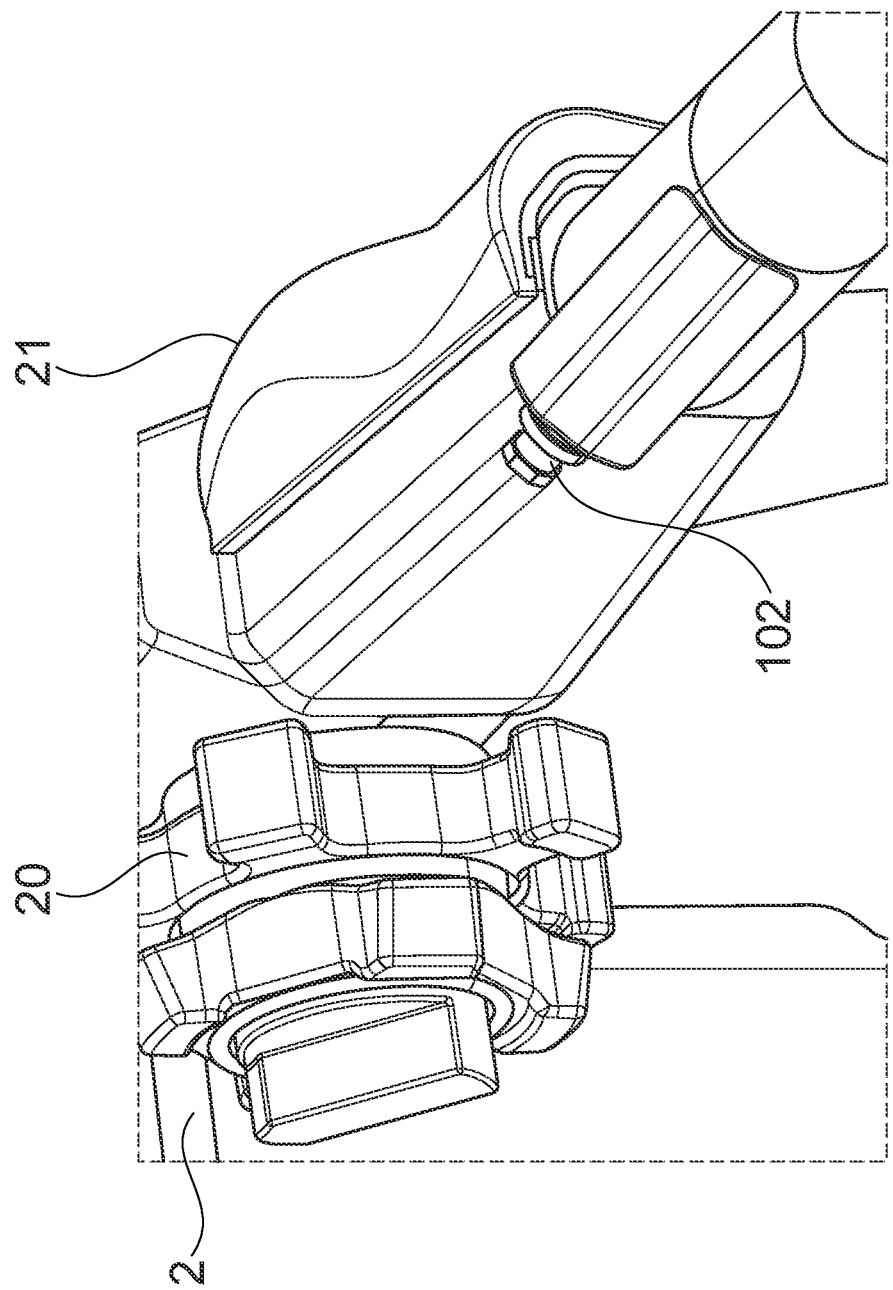
Figure 6B:
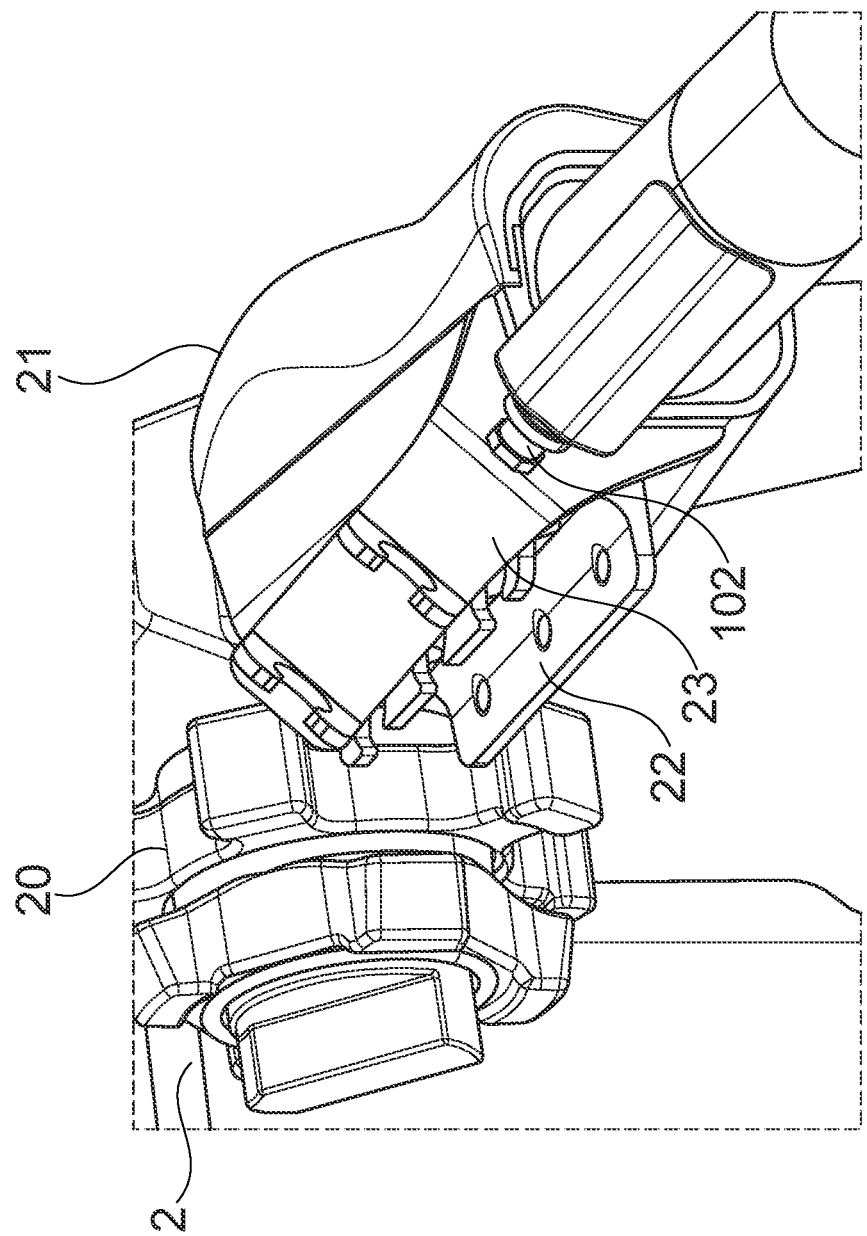

FIGS. 6a to 6c show partial sections of the mounting of an embodiment of the handle attachment 21 according to the invention. This is typically produced in at least two parts, one part representing an ergonomically formed handle 21, illustrated in FIG. 6a, which is mounted laterally on the handle 2 of the endoscope.

Opposite this, in FIG. 6b, a part with valve holder 22 and instrument holder 23, is mounted as counterpart and connected to the handle 21, for example via a click connection. The valve holder 22 is characterised by receptacles for three valves, the instrument holder 23 forms a receptacle for the two-way tube manifold 24, which is disposed above the proximal instrument channel opening 102.

FIG. 6c shows the final assembly state. The three valves for air, water and suction 5a, 5b, 5c are inserted into the corresponding receptacles on the valve holder 22 and connected to the air and water tubes 4a, 4b coming from the distal end of the endoscope shaft 1, as well as the suction tube 4d. The tubes emerging from the valves are connected to corresponding devices, by means of which the channels can be supplied with superatmospheric or subatmospheric pressure or water. During the endoscopic examination, the three valves 5a, 5b, 5d can be opened by the treating doctor by finger pressure. In an advantageous embodiment, these valves are inexpensive disposable products that can be discarded and exchanged after each examination. Furthermore, FIG. 6c shows the Y-shaped two-way tube manifold 24, which is plugged into the instrument holder 23, and is connected to the operating tube 4c projecting out of the proximal instrument channel opening 102. To the manifold legs emerging laterally, the suction tube 4d is connected; the straight-line legs of the manifold serves as access for the instrument 80 used in the course of the examination. The region between the distal end of the two-way tube manifold 24 and the proximal instrument channel opening 102, in which the operating tube 4c is exposed, is provided for cutting the operating tube 4c in the course of dismounting after endoscopy is completed. For cutting, a torch cutter should advantageously be used, which directly fuses the two cut ends in a sterile manner, in order to avoid escape of the contamination present in the operating tube 4c.

Figure 7:
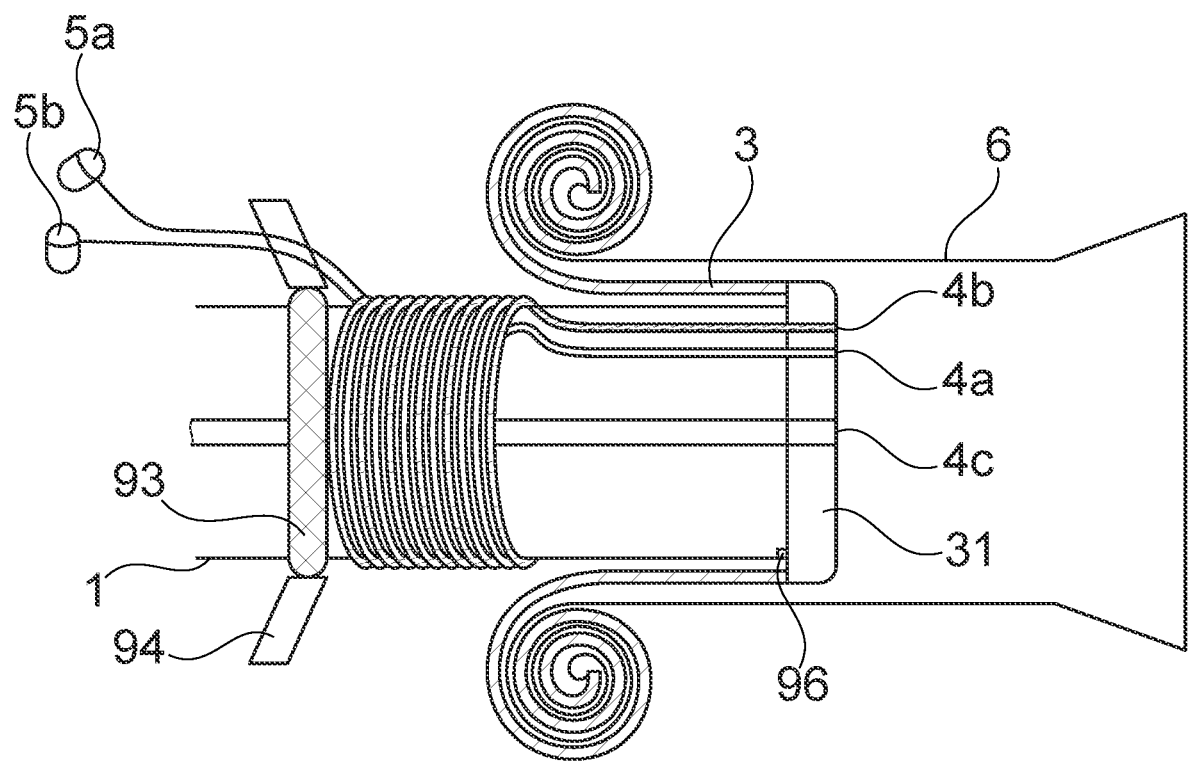
FIG. 7 shows an advantageous embodiment for user-friendly mounting of the protection device on the shaft.

FIG. 7 shows an embodiment of the contamination protection device preassembled during production for rapid and user-friendly attachment to the endoscope shaft 1. The goal is pursued of drawing the device onto the shaft 1 in one piece. To this end, the inner sleeve 3 and outer sleeve 6 lie on one another and are rolled up together as far as the cap 31. Behind this, the air and water tubes 4a, 4b, which open in the end face of the cap 31, are helically wound, the winding having a larger diameter than the shaft 1. Both tubes 4a, 4b are fixed on the clamp 94 and, with their proximal ends, connected to air valve 4a and water valve 5b. For mounting, the proximal end of the operating tube 4c, which also opens distally in the end face of the cap 31, is introduced into the distal instrument channel opening 101 and the entire structure mentioned above is pushed over the shaft tip onto the shaft 1 until the cap 31 engages on the distal clamping bracket 96 previously assembled. The clamp 94 is pushed over the proximal clamping bracket 93, which was also assembled previously, and in the process the inner sleeve 3 and outer sleeve 6 are unrolled. Subsequently only the proximal ends of the two sleeves 3, 6 are inserted into the clamps 94 and the clip 91 is closed around it, for fixing and sealing in the region of the proximal clamping bracket 93. Finally, the air valve 5a and water valve 5b are fastened on the handle attachment 21 and the operating tube projecting out of the proximal instrument channel opening 102 is connected to the two-way tube manifold 24.

Figure 8:
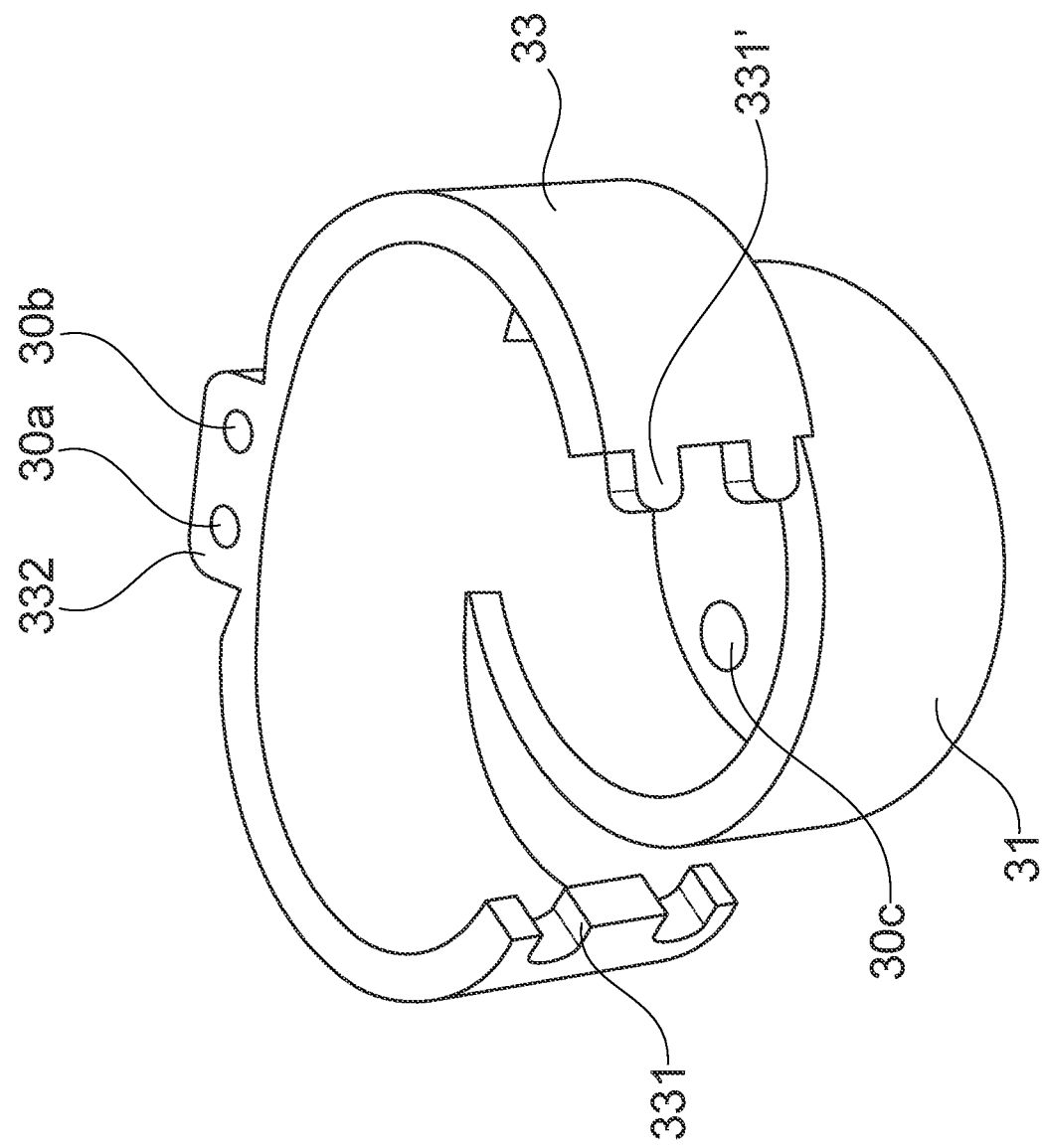
FIG. 8 shows an advantageous embodiment of a cap with click-closure.

FIG. 8 shows an advantageous embodiment of the cap 31, which is suitable for use without a distal clamping bracket.

For this purpose, a yoke-like gripper 33 is integrally formed on the proximal end of the cap 31.

Said clamp is produced from a suitably deformable polymer and can be bent together around the endoscope shaft and fixed via the click-closure 331, 331'. Air tube opening 30a and water tube opening 30bar are here disposed in a tubular form in a bridge 332, which connects the clamp 31 and gripper 33. The advantage of this embodiment consists in a small diameter in comparison to the variant with distal clamping bracket. The cap 31 shown in FIG. 8 with gripper 33 may advantageously also be used in a production-preassembled embodiment of the contamination protection device corresponding to FIG. 7. In addition, the distal end of the cap can also be made from an optically neutral shrink tube.

Figure 9:
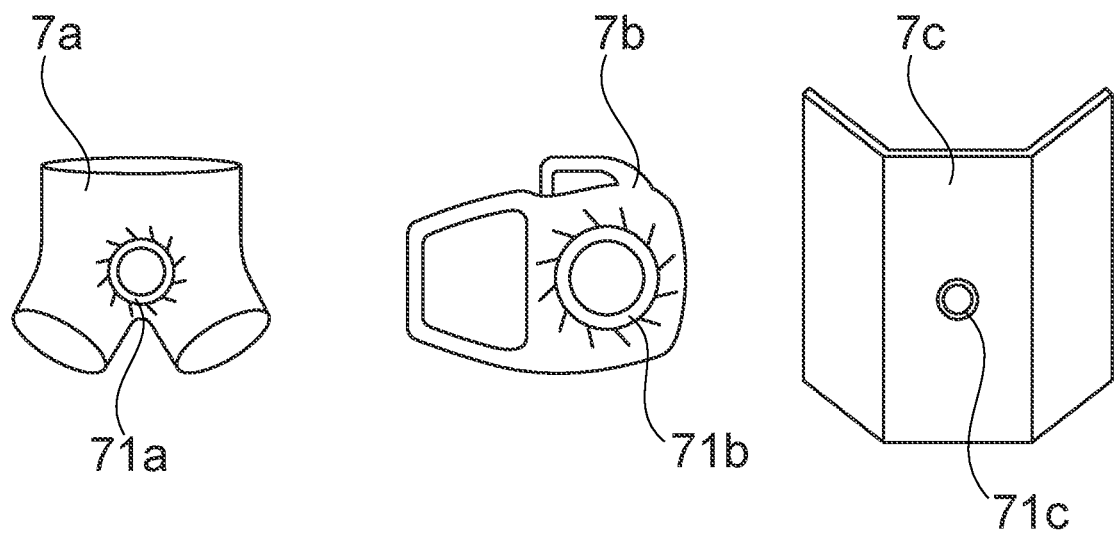
FIG. 9 shows diaper pants, bite ring and partition wall.

FIG. 9 shows objects which serve for patient-side connection of the distal end of the outer sleeve 6. This is, first, the diaper pants 7a according to the invention, which are used in coloscopies. These diaper pants 7a are put on by the patient to be examined and have an opening with a connection part 71a, which is suitable for positioning the body orifice to be examined, i.e. anus or ileostomy. To this connection part 71a, the outer sleeve 6 can be connected by means of the connection piece 61a, which is provided in an advantageous embodiment at its distal end, so that an airtight, watertight and germ-tight connection is produced. In the course of the coloscopy, the endoscope shaft 1, protected by the inner sleeve 3 is then pushed through the opening provided in the diaper pants 7a and into that body orifice of the patient that is to be examined. The intestinal contents emerging during the examination are thus prevented by the diaper pants 7a, on one hand, and the protective volume formed between the inner and outer sleeve 6, 3 on the other hand from escaping into the examination environment.

For gastroscopies the bite ring 7b according to the invention is used, on the opening of which is provided the connection part 71b. This serves in turn for patient-side connection of the outer sleeve 6 via the connection piece 61b. During the examination, to avoid or minimise the leaking of saliva from the patient's mouth corners and resulting contamination of the outer side of the outer sleeve 6, the bite ring 7b can be further extended with sections that enclose the patient's face or at least jaw part.

Alternatively to the diaper pants 7a or bite ring 7b, a partition wall 7c with opening and connection part 71c can be used, behind which the patient is positioned during the endoscopic examination. The treating doctor acts from the front side of the partition wall and is thus protected against direct contamination. In a further advantageous embodiment, the partition wall 7c may take the form of a cabin that is closed except for the passage opening, in which all the contamination removed from the patient during the examination can remain enclosed.

Figure 10:
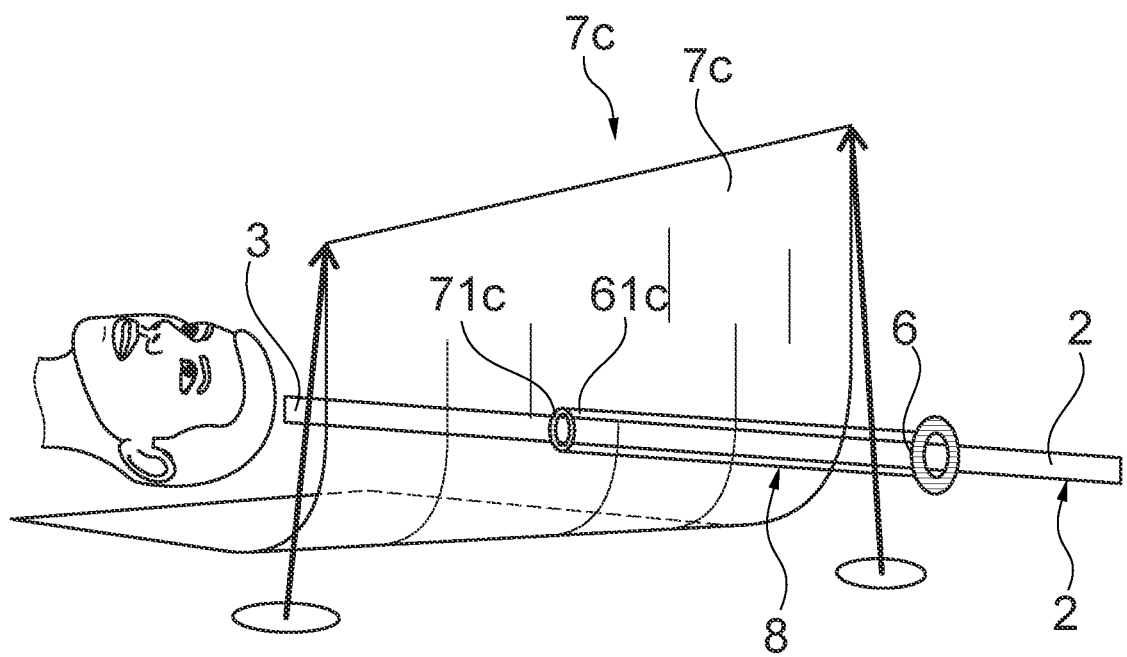
FIG. 10 shows an advantageous embodiment of a partition wall.

FIG. 10 shows an embodiment of the endoscope according to the invention in which a spanned film 7c is used as a separation between the patient and treating doctor. This film is provided with an opening on which the outer sleeve 6 is welded at its distal end, an airtight, watertight and germ-tight connection being thereby realised. The separating film 7c should be dimensioned such that it can be folded over and laid beneath the patient to be examined. By this means, all the contamination occurring during the examination is collected on the film and kept away from the rest of the examination environment, in particular the patient table.

Figure 11:
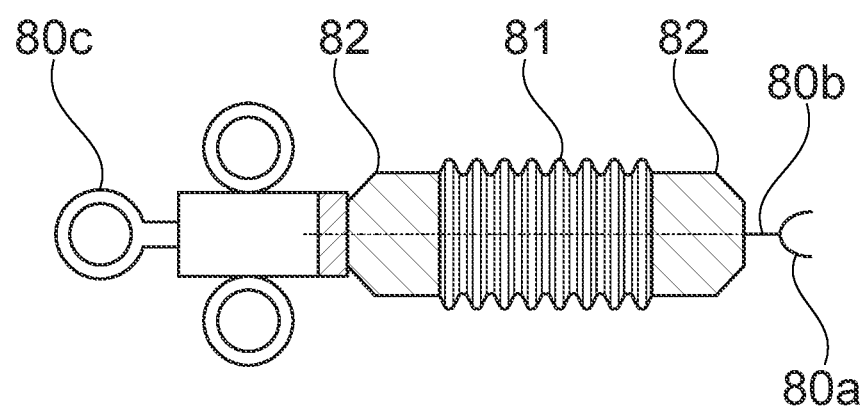
FIG. 11 shows an instrument with instrument protection according to the invention.

FIG. 11 shows the instrument protection 8 according to the invention along with a passed-through instrument 80, which usually consists of a micro-device 80a on an instrument Bowden cable 80b and can be operated with the operating element 80c. The instrument protection 8 consists of an instrument tube 81, which is pushed on here in the manner of a bellows and is limited at both ends by the instrument tube caps 82, on the end faces of which openings for passing through the instrument 80 are provided. During the endoscopic examination, the instrument protection 8, in the illustrated condition in which it is gathered together in the manner of a bellows, is connected to the proximal end of the straightlined leg of the two-way tube manifold 24. In order, after surgical intervention, to remove the contaminated part of the instrument 80 from the operating tube 4c without thereby releasing contamination, the end is drawn into the instrument tube 81, which, for this purpose is drawn out to its full length. The length of the instrument tube 81 is correspondingly to be dimensioned such that the micro-device 80a along with the Bowden cable 80b can be completely enveloped by it. After drawing of the instrument 80 into the instrument protection 8, the latter can be removed from the two-way tube manifold 24, all contamination now being retained in the interior of the instrument tube 81.

Figure 12A:
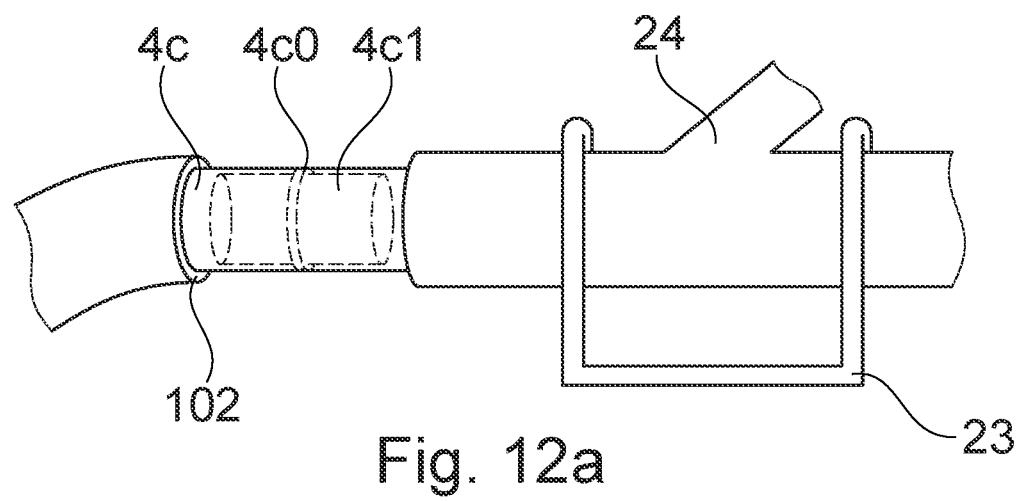
FIG. 12a-c shows an advantageous embodiment of the operating tube and cutting of the same.
Figure 12B:
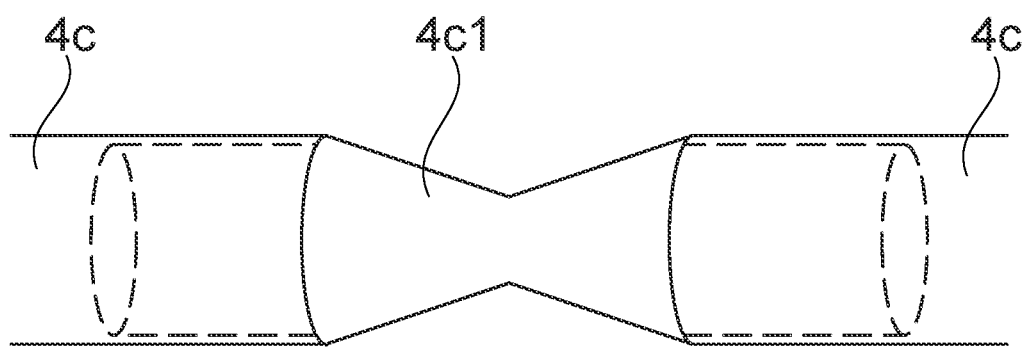
Figure 12C:
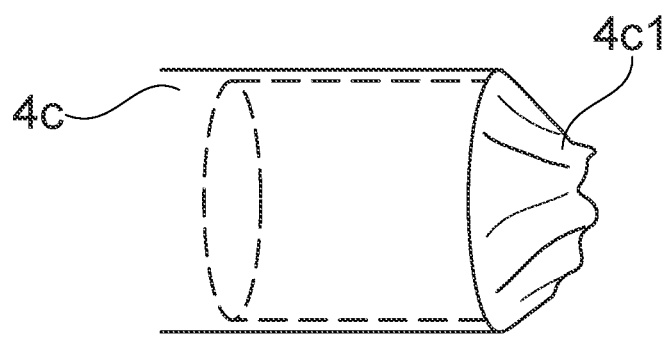

FIGS. 12a to 12c show an advantageous embodiment of the operating tube 4c according to the invention with a protective tube 4c1, which is compatible with contamination-protected dismounting.

FIG. 12a shows the mounted operating tube 4c, which projects out of the proximal instrument channel opening 102, and is connected to the distal end of the two-way tube manifold 24 in the instrument holder 23. In this freely accessible section, the operating tube 4c has a predetermined breaking point 4c0, for example in the form of a surrounding notch. Before and after this predetermined breaking point 4c0, the protection tube 4c1 is connected in an airtight, watertight and germ-tight manner to the outer side of the operating tube 4c, typically by means of a welded or adhesive bond.

FIG. 12b shows how the protection tube, after breaking of the predetermined breaking point 4c0 is drawn in length by pulling at the two cut ends of the operating tube 4c, and is thereby ultimately torn apart.

The polymeric material used for the protection tube 4c1 should have a significantly higher elongation at break than the material of the operating tube 4c, so that the torn-apart end sections, as shown in FIG. 12c, are plastically deformed to such an extent that they close the ends of the operating tube 4c in the manner of a pocket and protect it before escape of the contamination.

Instead of the embodiment shown here with protection tube 4c1 fastened on the outer side of the operating tube 4c, thus could also be mounted analogously in the interior of the operating tube.

Figure 13:
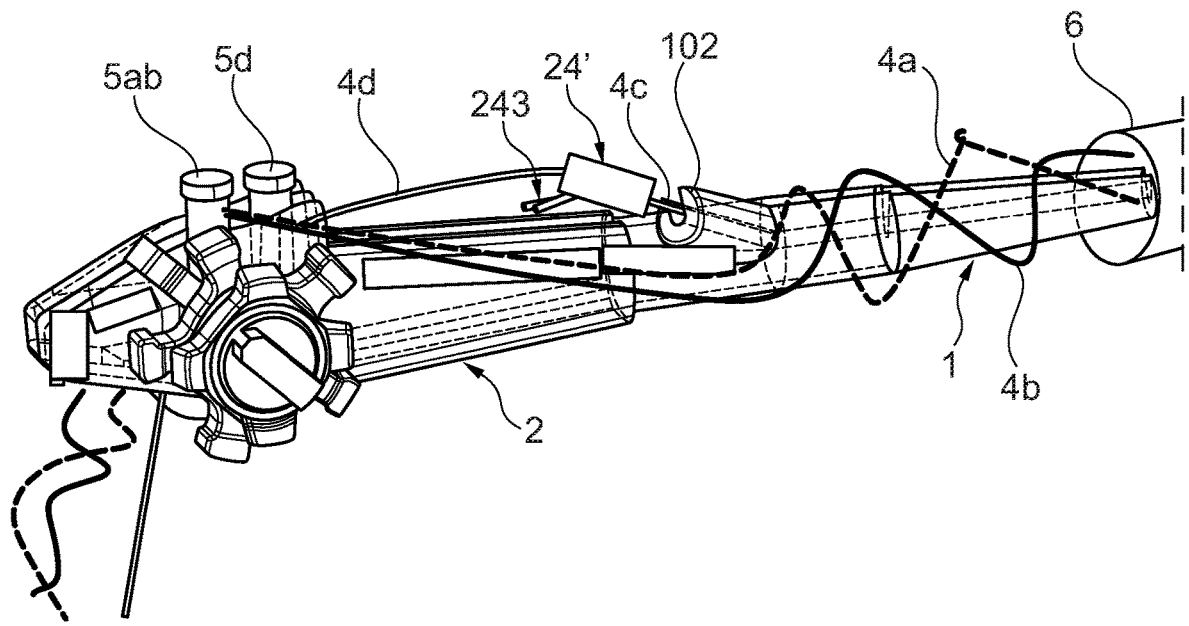
FIG. 13 shows an overall view of a further embodiment of the endoscope according to the invention with contamination protection device in which a two-way tube manifold is connected directly on the proximal instrument channel opening.

FIG. 13 shows a perspective overall view of a further embodiment of the endoscope according to the invention with contamination protection device in which the two-way tube manifold is connected directly on the proximal instrument channel opening.

Instead of using a handle attachment for fastening the two-way tube manifold and the valves, the tube manifold 24' is connected directly to the proximal instrument channel opening 102. The air and water valves are combined in a single valve 5ab, which is used together with the suction valve 5d in holders which are provided in the handle 2 for this purpose.

To the two-way tube manifold 24', first, the proximal end led out of the proximal instrument channel opening 102 of the operating tube 4c and, further, the suction tube 4d leading to the suction valve 5d are connected. The tubes for the compressed air 4a and the water supply 4b are wound around the shaft 1 for security and led to the combined air/water valves 5ab, and connected there.

Figure 14:
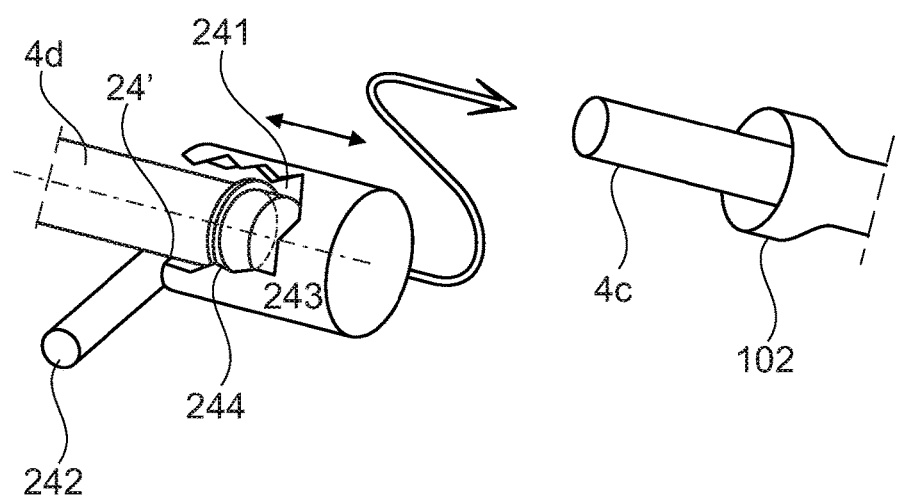
FIG. 14 shows a detail view of the two-way tube manifold of the embodiment from FIG. 13.
Figure 15:
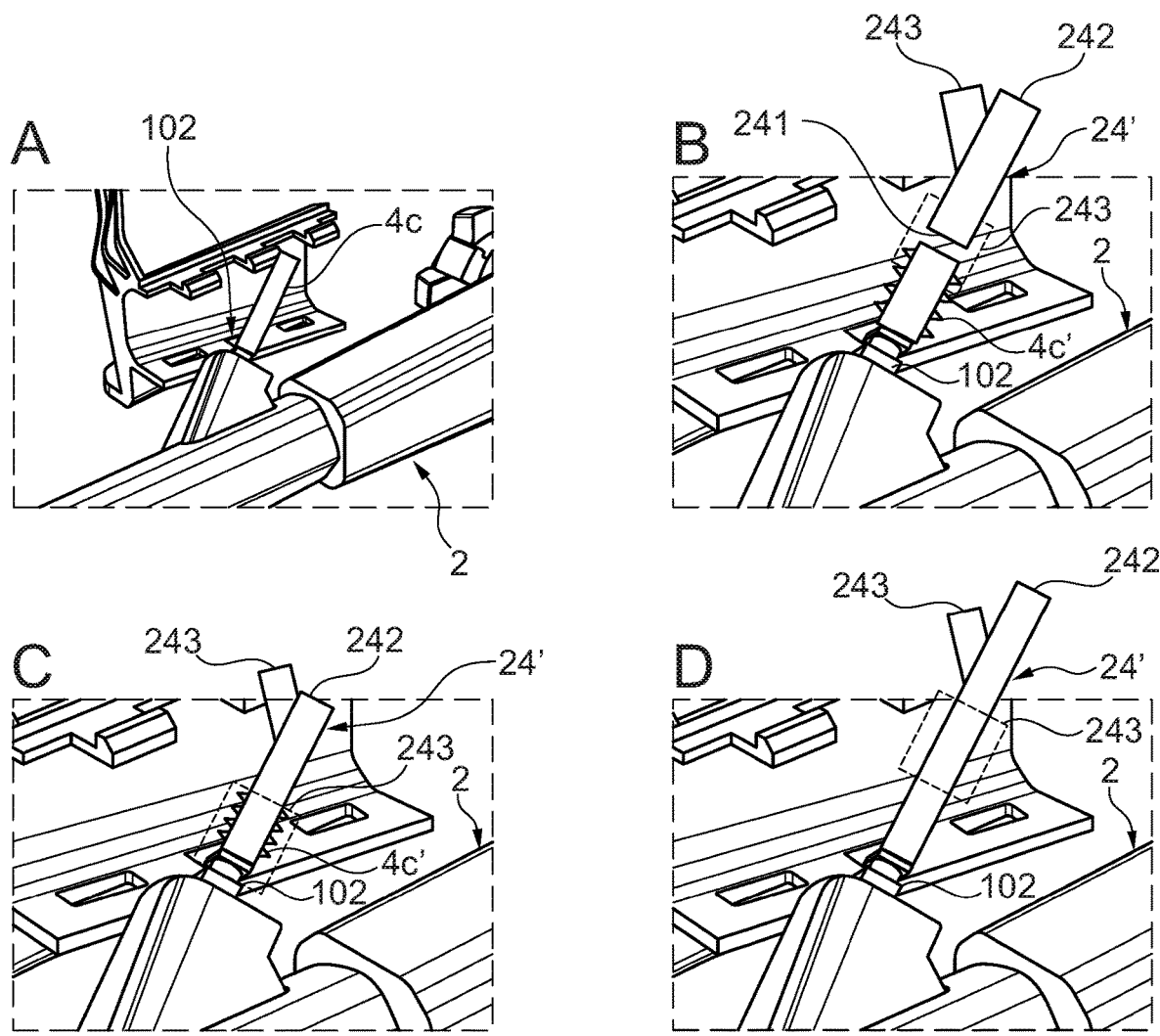
FIG. 15A-D shows an illustration of the connection process of the tube manifold according to the embodiment from FIGS. 13 and 14.

FIG. 14 schematically shows in detail the two-way tube manifold suitable for direct connection to the instrument channel opening of the embodiment shown in FIG. 13.

The Y-shaped two-way tube manifold 24' has three ends or connections. With the distal end 241, which may in particular be conically formed, it can be plugged into the proximal end 242 of the operating tube 4c led out of the instrument channel opening 102. At one of the two proximal ends, the suction tube 4d is connected. The other end 242 is open and serves as instrument access.

For fastening to the proximal instrument channel opening, the tube manifold 24' is equipped with a ring nut 243, which is seated on the tube manifold 24' so as to be axially displaceable. A collar 244, which is radially prominent and is integrally formed on the distal end 241 interacts with a stop on the ring nut 243, in order. after fixing of the ring nut on a corresponding connection means of the proximal instrument channel opening 102, to fasten the tube manifold thereon. The instrument channel opening 102 may for this purpose have a widespread Luer lock connection.

The (partial) FIGS. 15A-D illustrate the procedure during direct connection of a tube manifold of the embodiment according to FIGS. 13 and 14.

First, as shown in partial Figure A, the operating tube 4c is pushed a sufficient distance out of the proximal instrument channel opening 102. Then the two-way tube manifold 24' is connected to the distal end 41 thereof by plugging in the operating tube, partial Figure B. The operating tube 4c is designed here such that, due to the compressive forces exerted by plugging in the two-way tube manifold 24', the proximal operating tube end is compressed in the manner of a bellows and the bellows section 4c' is formed in this manner. Partial figure C shows the step in which the ring nut 243 of the tube manifold 24' is connected with the aid of a connection means, in this case a Luer lock connection, to the proximal instrument channel opening. The endoscope is now ready for an examination or an operation. After its end, as indicated in partial figure D, the two-way tube manifold 24' is released again and, together with the operating channel of the proximal instrument channel openings 102, pulled off, whereby the bellows section 4c' of the operating channel 4c unfolds again. By means of a torch cutter, the operating tube can be cut in one step and sealed and thus drawn, in a contamination free condition, distally out of the instrument channel.

Figure 16:
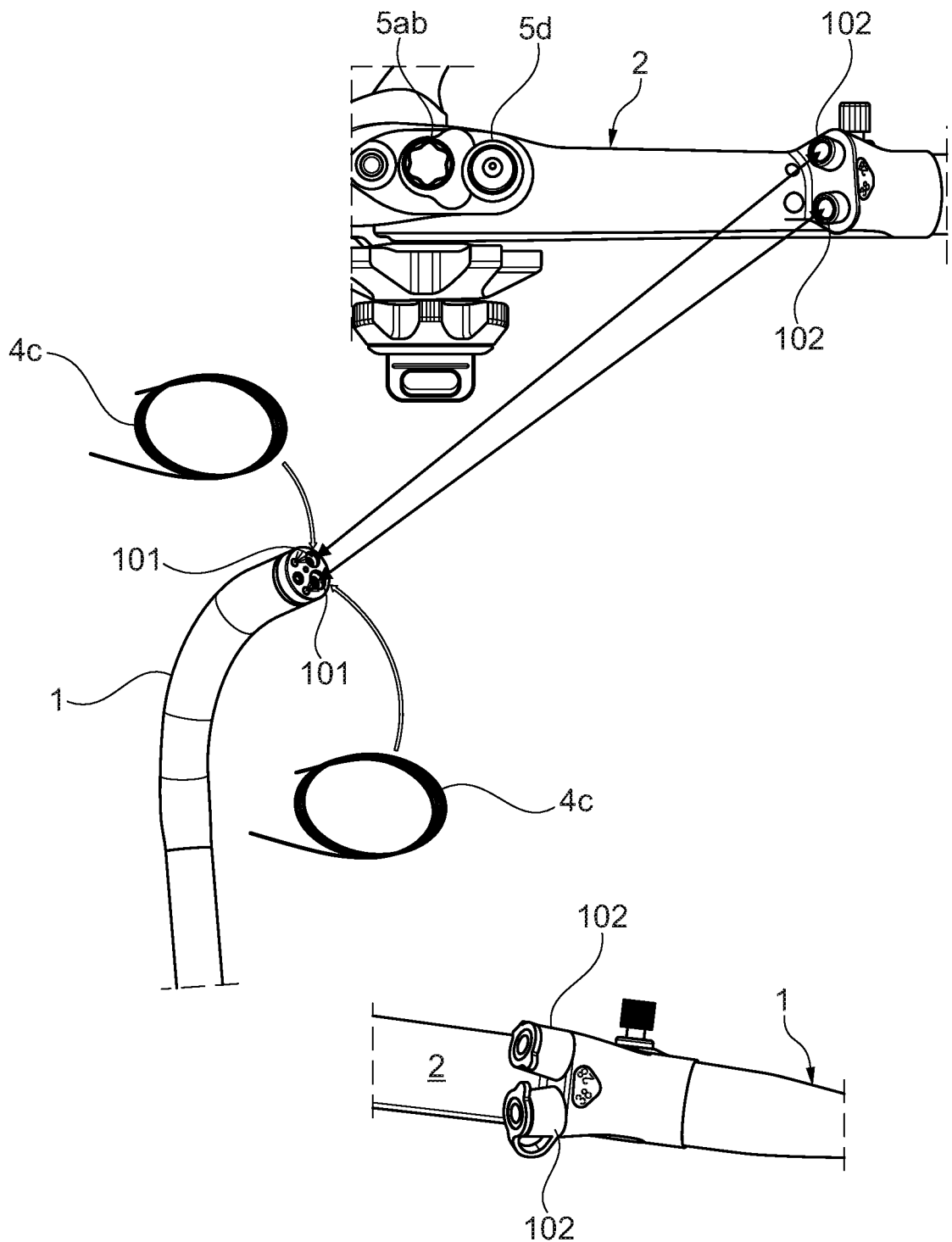
FIG. 16 shows views of a further embodiment of the endoscope according to the invention with two instrument channels and operating tubes.

FIG. 16 shows a further embodiment of an endoscope according to the invention with two instrument channels and correspondingly two operating tubes.

The distal end of the shaft 1, shown in the left-hand partial figure, has two distal instrument channel openings 101, into which, within the scope of the contamination protection according to the invention, an operating tube 4c in each case is to be pushed. The two instrument channels of the endoscope shown here open proximally into two corresponding instrument channel openings 102, partial figure top right. This partial figure also shows the valve holders with valves 5ab for air and water, as well as 5d for suction. The partial figure below right shows the instrument channel openings 102 sealed with protective caps.

LIST OF REFERENCE CHARACTERS

1 Shaft
10 Instrument channel
101 Instrument channel opening, distal
102 Instrument channel opening, proximal
11 Optics
12 Lighting device
13 Nozzle
2 handle
20 Operating element Shaft tip angling
21 Handle attachment
22 Valve holder
23 Instrument holder
24, 24' 2-way tube manifold
241 Distal end of 24 and 24'
242 Instrument opening of 24'
243 Ring nut
3 Inner sleeve
30 Inner sleeve end face
30a Air-tube opening
30b Water-tube opening
30c Operating tube opening
31 Cap
32 Fabric tube
33 Gripper
331, 331' Click-closure
332 Bridge
4a Air tube
4b Water tube
4c Operating tube
4c' Bellows section
4c0 Predetermined breaking point
4c1 Protective tube
4d Suction tube
5a Air valve
5b Water valve
5ab Combined air and water valve
5d Suction valve
6 Outer sleeve
61a,b,c Connection pieces
7a Diaper pants
7b Bite ring
7c Partition wall
71a,b,c Connection pieces
8 Instrument protection
81 Instrument tube
82 Instrument tube cap
80 Instrument
80a Micro unit
80b Instrument Bowden cable
80c Operating element instrument
91 Clip
92 Gasket, proximal
93 Clamping bracket, proximal
94 Clamp
95 Gasket, proximal
96 Clamping bracket, proximal
960 Positioning aid

The invention claimed is:

1. An endoscope with a contamination protection device for protecting the endoscope as well as a person performing an examination on a patient using the endoscope from contamination, comprising:
   a rigid or flexible shaft having a tip on which optics, a lighting device and a nozzle are configured to be disposed, a handle adjoined to a proximal end of the rigid or flexible shaft, an inner sleeve made of an airtight and watertight material that is impervious to pathogens for protecting the rigid or flexible shaft from contamination, the airtight and watertight material of the inner sleeve being flexible and compressible so that the inner sleeve is configured to be rolled-up or folded and unrolled or unfolded relative to the rigid or flexible shaft, the inner sleeve being closed at one distal end of the inner sleeve and having an optically transparent region on an end face of the inner sleeve, and the inner sleeve being configured to be unrolled or unfolded over the rigid or flexible shaft to cover the rigid or flexible shaft in an airtight, watertight and germ-tight manner, at least one air tube and a water tube, which terminate openly at the distal end of the inner sleeve and are connected thereto and are positioned between the rigid or flexible shaft and the inner sleeve, and an outer sleeve made of an airtight and watertight material that is impervious to pathogens, the airtight and watertight material of the outer sleeve being flexible and compressible so that the outer sleeve is configured to be rolled up or folded and unrolled or unfolded relative to the inner sleeve and configured to envelop the inner sleeve, the outer sleeve being connected in an airtight, watertight and germ-tight manner only to a proximal end of the inner sleeve at the proximal end of the rigid or flexible shaft, and the outer sleeve extending beyond the tip of the rigid or flexible shaft in a frustum shape;

wherein when the inner sleeve is unrolled or unfolded over the rigid or flexible shaft and the outer sleeve envelops the inner sleeve, the inner sleeve and the outer sleeve form a protection volume between a body orifice of the patient to be examined and the proximal end of the rigid or flexible shaft for collecting body fluids released by the patient in a course of the examination, the protection volume being spanned between an outer surface of the inner sleeve and an inner surface of the outer sleeve from the handle to a distal end of the outer sleeve.

2. The endoscope according to claim 1, wherein at the distal end of the outer sleeve:
a first connecting piece is integrally formed, and diaper pants for the patient to be coloscopically examined are provided, which have an opening with a first receiving part, to which the first connecting piece of the outer sleeve is connected in an airtight, watertight and germ-tight manner, and/or
a second connecting piece is integrally formed, and a bite ring for the patient to be gastroscopically examined is provided, which has an opening with a second receiving part, to which the second connecting piece of the outer sleeve is connected in an airtight, watertight and germ-tight manner, and/or
a third connecting piece is integrally formed, and a separating wall or a cabin for the patient to be examined behind is provided, which has an opening with a third receiving part, to which the third connecting piece of the outer sleeve is connected in an airtight, watertight and germ-tight manner.

3. The endoscope according to claim 1, wherein a film with an opening is welded onto a distal end of the outer sleeve in an airtight, watertight and germ-tight manner, and, by means of a holding device, is spanned in front of the patient to be examined.

4. The endoscope according to claim 1, wherein the airtight and watertight material of the inner sleeve and the outer sleeve is flexible and compressible so that the inner and the outer sleeves are configured to be rolled up or folded in a manner of a bellows.

5. The endoscope according to claim 1, wherein:
in the rigid or flexible shaft, there runs at least one instrument channel, which opens at the tip of the rigid or flexible shaft into a distal instrument channel opening and, at the handle, in a proximal instrument channel opening,
the end face of the inner sleeve has an operating tube opening that is congruent with the distal instrument channel opening, and
the operating tube opening has an adjoining operating tube, which is positioned in the at least one instrument channel and projects out of the distal instrument channel opening.

6. The endoscope according to claim 5, wherein the adjoining operating tube has, in a section of the adjoining operating tube that projects out of the distal proximal instrument channel opening, a predetermined breaking point, and in that a protective tube, made of a polymeric material, which has a higher elongation at break than a material of the operating tube, is fastened on an outer or inner side of the operating tube such that the protective tube is connected upstream as well as downstream of the predetermined breaking point in a manner that is airtight, watertight and germ-tight.

7. The endoscope according to claim 1, wherein: the handle has valve holders into which an air valve and a water valve or a combined air/water valve integrated in a valve block, as well as a suction valve can be plugged, and the endoscope further comprises a two-way tube manifold, which is plugged at a distal, in particular conically designed end into a proximal end of the adjoining operating tube, the two-way tube manifold having an instrument opening and a ring nut which is movable axially relative to the tube and by means of which a proximal instrument channel opening of the endoscope can be fastened.

8. The endoscope according to claim 1, further comprising a handle attachment in which are retained:
an air valve and a water valve in a valve holder,
an instrument holder with, inserted therein, a 2-way tube manifold, on a distal end of which an operating tube is connected,
a suction valve, and
a suction tube, which is connected on a first proximal end of the 2-way tube manifold and on the suction valve.

9. The endoscope according to claim 8, wherein at a second proximal end of the 2-way tube manifold, an instrument protector is connected, which consists of an instrument tube, which can be gathered together in a manner of a bellows, and, on each end, has an instrument protection cap with an opening at its end, and has a length that is larger than one length of the operating tube.

10. The endoscope according to claim 1, wherein the inner sleeve and/or the outer sleeve on the proximal end of the rigid or flexible shaft is fastened on an outer surface of the rigid or flexible shaft, in particular in that it is pressed, by means of a clip or a rubber ring, on a proximal clamping bracket, which is disposed on the outer surface of the rigid or flexible shaft and has a proximal seal placed below it, and has passages for the at least one of the air tube and the water tube.

11. The endoscope according to claim 1, wherein the distal end of the inner sleeve is designed as an essentially hollow cylindrical cap with an open end face, which, at an end face opposite the open end face, has an air tube opening and a water tube opening, and on which the air tube and the water tube are integrally formed:
- a yoke-like gripper with a click-closure being integrally formed on a cap and a fastening of the cap on a distal end of the rigid or flexible shaft being ensured in that the cap is mounted on a distal clamping bracket that is disposed on an outer surface of the rigid or flexible shaft and is underlaid by a distal gasket and has passages for the air tube and water tube, or
- for clamping on the distal end of the rigid or flexible shaft, axially running elastic branches are integrally formed on an open end face of the cap.

12. The endoscope according to claim 1, wherein the inner sleeve and the outer sleeve are made in one piece, that is to say that the airtight, watertight and germ-tight connection of the outer sleeve to the proximal end of the inner sleeve are already provided during manufacturing, for example by welding and/or the inner sleeve is underlaid by a fabric tubing and/or the outer sleeve encloses the handle and a handle attachment.

13. The endoscope according to claim 12, wherein a two-way tube manifold is integrated into a section of the outer sleeve that encloses the handle and the handle attachment.

14. A method for mounting the contamination protection device for the endoscope according to claim 1 to prepare the endoscope for a contamination-protected endoscopic examination in which the rigid or flexible shaft of the endoscope is inserted into a body orifice to be examined, comprising the steps:
- applying to the optically transparent region of the inner sleeve a substance that produces optical contact with the optics of the endoscope,
- plugging a handle attachment onto the handle,
- introducing the distal end of the rigid or flexible shaft into the inner sleeve while the inner sleeve is in a rolled-up folded state,
- completely covering the rigid or flexible shaft with the inner sleeve by unrolling or unfolding the inner sleeve over the rigid or flexible shaft and at least one of the air tube and the water tube positioned thereon,
- connecting proximal ends of the at least one of the air tube and the water tube with an air valve and a water valve on the handle attachment,
- pushing the outer sleeve, in a rolled-up or folded state, over the inner sleeve after the inner sleeve is unrolled or unfolded over and covers the rigid or flexible shaft and fastening the outer sleeve in an airtight, watertight and germ-tight manner on the proximal end of the inner sleeve, and
- unrolling or unfolding the outer sleeve over the rigid or flexible shaft so the outer sleeve extends beyond the tip of the rigid or flexible shaft in a frustum shape.

15. The method of claim 14, wherein a first or second or third connection piece of the outer sleeve is connected to a first or second or third connection part, respectively.

16. The method of claim 14, wherein for fastening and connecting the inner sleeve and the outer sleeve, the following steps are performed:
- bonding of a proximal gasket onto an outer surface of a proximal end of the rigid or flexible shaft,
- applying a proximal clamping bracket on the proximal gasket,
- bonding of a distal gasket onto an outer surface of the distal end of the rigid or flexible shaft,
- mounting a distal clamping bracket on the distal gasket using a positioning aid,
- positioning the at least one of the air tube and the water tube in passages on the distal clamping bracket,
- plugging a cap onto the distal clamping bracket,
- positioning the air tube and water tube in passages on the distal clamping bracket,
- positioning the proximal ends of the inner sleeve and the outer sleeve over the proximal clamping bracket, and
- clamping the inner sleeve and the outer sleeve between the proximal clamping bracket and a clip or a rubber ring.

17. The method of claim 16, wherein before introduction of the distal end of the rigid or flexible shaft into the inner sleeve, a proximal end of an operating tube is introduced into a distal instrument channel opening to an extent that the proximal end of the operating tube projects out of a proximal instrument channel opening and in that subsequently:
- the proximal end of the operating tube is connected to a distal end of a 2-way tube manifold,
- a first proximal end of the 2-way tube manifold is connected to a suction valve by means of a suction tube, and
- a second proximal end of the 2-way tube manifold is connected to an instrument protector, which is folded in a manner of a bellows.

18. The method of claim 17, wherein the 2-way tube manifold is fastened by means of a ring nut directly on the proximal instrument channel opening.

19. The method of claim 16, wherein the contamination protection device comprises a first contamination protection device and the contamination-protected endoscopic examination comprises a first contamination-protected endoscopic examination in which a last step of the examination includes removing the rigid and flexible shaft of the endoscope out of the examined body orifice; and further comprising the following steps for preparing the endoscope for a second contamination-protected endoscopic examination:
- separating the outer sleeve in a region of the distal end as well as from the air tube and the water tube in a region of the handle,
- removing and disposing of the first contamination protection device,
- providing a second contamination protection device according to claim 1, and mounting the second contamination protection device on the endoscope according to the steps in claim 16.

20. The method of claim 19, wherein the proximal clamping bracket and the distal clamping bracket are not removed during removal of the first contamination protection device and remain on the rigid or flexible shaft for fastening and connecting the inner sleeve and the outer sleeve of the second contamination protection device during preparation of the endoscope for the second contamination-protected endoscopic examination.

21. The method of claim 14, wherein the material of the inner sleeve and the outer sleeve is flexible and compressible so that the inner and the outer sleeves are configured to be rolled up or folded in a manner of a bellows.

22. An endoscope with a contamination protection device for protecting from contamination the endoscope as well as a person performing an examination on a patient using the endoscope, comprising:
- a shaft having a tip on which optics, a lighting device and a nozzle are configured to be disposed;
- a handle adjoining the shaft;
- an inner sleeve that is closed at one distal end of the inner sleeve and has an optically transparent region on an end face of the inner sleeve, the inner sleeve being made of an airtight and watertight material that is impervious to pathogens for protecting the shaft from contamination, and the airtight and watertight material of the inner sleeve being flexible and compressible so that the inner sleeve is configured to be manipulated relative to the shaft between (i) a first position in which the inner sleeve is disposed over and covers the shaft in an airtight, watertight and germ-tight manner and (ii) a second position in which the inner sleeve is not disposed over and does not cover the shaft;
- at least one air tube and a water tube, which terminate openly at the distal end of the inner sleeve and are connected thereto and are positioned between the shaft and the inner sleeve; and
- an outer sleeve made of an airtight and watertight material that is impervious to pathogens, the airtight and watertight material of the outer sleeve being flexible and compressible so that the outer sleeve is configured to be manipulated relative to the inner sleeve between (i) a first position in which the outer sleeve envelops the inner sleeve and (ii) a second position in which the outer sleeve does not envelop the inner sleeve, and the outer sleeve extending beyond the tip of the shaft in a frustum shape and being connected in an airtight, watertight and germ-tight manner only to a proximal end of the inner sleeve at the proximal end of the shaft;
- wherein in the first position of each of the inner sleeve and the outer sleeve, the inner sleeve and the outer sleeve form a protection volume between a body orifice of the patient to be examined and a proximal end of the shaft for collecting body fluids released by the patient in the course of the examination, the protection volume being spanned by the inner sleeve and by the outer sleeve from the handle to the end face of the inner sleeve.

* * * * *